United States Patent
Reisinger et al.

(10) Patent No.: US 9,677,059 B2
(45) Date of Patent: Jun. 13, 2017

(54) ENDOGLUCANASES WITH IMPROVED PROPERTIES

(71) Applicant: CLARIANT PRODUKTE (DEUTSCHLAND) GMBH, Frankfurt am Main (DE)

(72) Inventors: Christoph Reisinger, Munich (DE); Joerg Claren, Munich (DE); Isabel Unterstrasser, Rimsting (DE); Aleksandra Mitrovic, Graz (AT); Karlheinz Flicker, Cologne (DE); Gabi Gebhardt, Altheim (DE)

(73) Assignee: CLARIANT PRODUKTE (DEUTSCHLAND) GMBH, Frankfurt/Main (DE)

( * ) Notice: Subject to any disclaimer, the term of this patent is extended or adjusted under 35 U.S.C. 154(b) by 17 days.

(21) Appl. No.: 14/397,980

(22) PCT Filed: Apr. 30, 2013

(86) PCT No.: PCT/EP2013/058985
§ 371 (c)(1),
(2) Date: Oct. 30, 2014

(87) PCT Pub. No.: WO2013/164340
PCT Pub. Date: Nov. 7, 2013

(65) Prior Publication Data
US 2015/0175987 A1   Jun. 25, 2015

(30) Foreign Application Priority Data
May 2, 2012   (EP) .................................... 12166458

(51) Int. Cl.
*C12N 9/42* (2006.01)
*C12P 19/02* (2006.01)
*C12P 19/14* (2006.01)

(52) U.S. Cl.
CPC ............ *C12N 9/2437* (2013.01); *C12P 19/02* (2013.01); *C12P 19/14* (2013.01)

(58) Field of Classification Search
None
See application file for complete search history.

(56) References Cited

U.S. PATENT DOCUMENTS 5,912,157 A   6/1999   von der Osten et al.

FOREIGN PATENT DOCUMENTS

| WO | 2007115723 A2 | 10/2007 |
| WO | 2011153516 A2 | 6/2011 |
| WO | 2012036810 A2 | 3/2012 |

OTHER PUBLICATIONS

Ngo et al. In the Protein Folding Problem and Tertiary Structure Prediction, 1994, Merz et al. (ed.), Birkhauser, Boston, MA, pp. 433 and 492-495.*
Chen et al. (Genbank Accession No. EF185865.1 Jan. 2007).*
Gonzalez et al. (Applied Microbiology and Biotechnology vol. 38, pp. 370-375, 1992).*
Dzogbefia et al. (Scientific and Essay vol. 3, pp. 365-369, Aug. 2008).*
"Trichoderma reesei endoglucanase;" May 10, 2012, XP002680452; retrieved from EBI accession No. GSP:AZU33761.
Karlsson, J., et al.; "Enzymatic properties of the low molecular mass endoglucanases Cel12A (EG III) and Cel45A (EG V) ofTrichoderma reesei;" Biotechnol. vol. 99, No. 1, Oct. 9, 2002, pp. 63-78.
Karlsson, J., at al.; "Enzymatic degradation of carboxymethyl cellulose hydrolyzed by the endoglucanasesCel5A, Cel7B, and Cel45A from Humicola insolens and Cel7B, Cel12A and Cel45Acore from Trichoderma reesei;" Biopolymers vol. 63, No. 1, Jan. 2002, pp. 32-40 (Abstract Only).
Henrissat, B., et al.; "Synergism of Cellulases from Trichoderma reesei in the Degradation of Cellulose;" Nature Biotechnology vol. 3, 1985, pp. 722-726 (Abstract Only).
Dominguez, J.M., et al.; "Mechanisms of thermoinactivation of endoglucanase 1 from Trichoderma reesei QM 9414;" Biochem J. vol. 287, Oct. 15, 1992, pp. 583-588.
Zhang, N., et al.; "Improving tolerance of Candida antarctica lipase B towards irreversible thermal inactivation through directed evolution;" Protein Eng. vol. 16, No. 8, Aug. 2003, pp. 599-605.
Cantarel, B., at al.; "The Carbohydrate-Active-Enzymes database (CAZy): an expert resource for Glycogenomics;" Nucleic Acids Research 2009; vol. 37, Issue D233-D238.
Schomburg, I., et al.; "Enzyme data and metabolic information: BRENDA, a resource for research in biology, biochemistry, and medicine;" Gene Fund. Dis., vol. 3-4, 2000, pp. 109-118 (Abstract Only).
Larkin, M.A., et al; "ClustalW and ClustalX version 2;" Bioinformatics vol. 23, No. 21, 2007, pp. 2947-2948.
Livingstone, C.D., et al.; Protein sequence alignments: a strategy for the hierarchical analysis of residue conservation; Comput.Appl Biosci. vol. 9, 1993, pp. 745-756 (Abstract Only).
Taylor, W.R.; "The classification of amino acid conservation;" J.Theor.Biol. vol. 119, 1986, pp. 205-218 (Abstract Only).
Ho, S.N.; et al.; "Site-directed mutagenesis by overlap extension using the polymerase chain redaction;" Gene vol. 77, 1989, pp. 51-59, XP 000272761 (Abstract Only).
Liu, Z.; et al. Chembiochem. vol. 9, No. 1, Jan. 4, 2008, pp. 58-61.
Lin-Cereghino, J., et al.; Condensed protocol for competent cell preparation and transformation of the methylotrophic yester Pichia pastoris; Biotechniques vol. 38, 2005, pp. 44-48.

(Continued)

*Primary Examiner* — Richard Hutson
(74) *Attorney, Agent, or Firm* — Gianna Julian-Arnold; Saul Ewing LLP

(57) ABSTRACT

The present invention relates to thermostable endoglucanases, particularly to proteins having endoglucanase activity which comprises an amino acid sequence having at least 96% identity to SEQ. ID NO.: 2, and proteins having endoglucanase activity which belongs to the GH7 class and which shows active thermostabilization.

10 Claims, 3 Drawing Sheets

(56) References Cited

OTHER PUBLICATIONS

Zhu, Y.S., et al.; "Induction and regulation of cellulase synthesis in Trichoderma pseudokoningii mutants EA3-867 and N2-78;" Enzyme and Microbial Technology, Stoneham, MA, US, vol. 4, No. 1, Jan. 1, 1982 (Jan. 1, 1982), pp. 3-12, XP023678002, ISSN: 0141-0229, DOI: 10.1016/0141-0229(82)90003-5 [retrieved on Jan. 1, 1982].

Eriksson, T., et al.; "A model explaining declining rate in hydrolysis of lignocellulose substrates with cellobiohydrolase I (Cel7A) and Endoglucanase I (Cel7B) of Trichoderma reesei", Applied Biochemistry and Biotechnology, Humana Press, Inc, United States, vol. 101, No. 1, Apr. 1, 2002 (Apr. 1, 2002), pp. 41-60, XP008103337, ISSN: 0273-2289, DOI: 10.1385/ABAB:101:1:41 [retrieved on Jun. 1, 2007].

\* cited by examiner

SEQUENCE LISTING

<160> NUMBER OF SEQ ID NOS: 16

<210> SEQ ID NO 1
<211> LENGTH: 1323
<212> TYPE: DNA
<213> ORGANISM: artificial
<220> FEATURE:
<223> OTHER INFORMATION: artificial construct

<400> SEQUENCE: 1

```
tctctgcagc caggaacttc tactccagag gtgcacccaa agctgaccac ctacaagtgt      60
accacctctg gtggttgtgt tgctcagaac acctatgttg ttctggactg gaactacaga     120
tggatccacg acgccaacta caactcttgt accgtgaacg gtggtgtcaa cactactctg     180
tgtccagacg aggctactgg tagcaagaac tgcttcatcg agggtgttga ctacgctgct     240
tctggtgtta ctgccaatgg ttctaccttg accctgaacc agtacatgcc atcttcctct     300 ggcgttaca cttctgtgtc gccaagactg tacttgttgg gtccagacgg taagtacgtt     360
atgctgaagc tgaacggaca ggagctgtct tttgacgttg acctgtctgc tttgccatgt     420
ggagagaacg cttctctgta cctgtctcag atggacgaga acgtggagc taaccagtac     480 aacaccgccg gtgctaacta cggttctggt tactgtgacg cccagtgtcc agttcagact     540
tggagaaacg gaaccctgaa cacttctggc cagggattct gctgtaacga gatggacatc     600
ttggagggaa actctagagc taacgctctg accccacact cttgtaatgc taccgcttgt     660
gactctgctg gttgcggttt taacccatac cgctcgggtt acccaaacta ctttggccca     720
ggtggcactg ttgacaccct cgaagccatt accatcatca cccagttcaa caccgacaac     780
ggttctccat ctggtaacct ggtgtcgatc accagaaagt acagacagaa cggcgttgac     840
atcccatctg ctaaaccagg tggcgacacc attcgtctct gtccatctgc tctctacttac    900 ggtgattgg ctaccatggg aaaggctctg tccgagggaa tggtgctgat cttctcgatc     960
tggaacgaca actcgcagta catgaactgg ctggactctg gtgatgctgg tccatgttct    1020
tctaccgagg gcaacccatc taacatcctg gctaacaacc ctggtactca cgtggtgtac    1080
tcgaacatta tgggggcga cattggttct accaccaact ctaccggtgg taacccacca    1140
ccaccacctg catcttctac caccttctcg accgccagaa gatcgtctac ctcctcttct    1200
tctccatctt gtatccagac tcactgggtt cagtgtggtg gtattggcta caccggctgt    1260
aagacctgta cctctggaac cacttgccag tacagcaacg actactactc tcagtgcctg    1320
tga                                                                  1323
```

<210> SEQ ID NO 2
<211> LENGTH: 440
<212> TYPE: PRT
<213> ORGANISM: artificial
<220> FEATURE:
<223> OTHER INFORMATION: artificial construct

<400> SEQUENCE: 2

Ser Leu Gln Pro Gly Thr Ser Thr Pro Glu Val His Pro Lys Leu Thr
1               5                   10                  15

Thr Tyr Lys Cys Thr Thr Ser Gly Gly Cys Val Ala Gln Asn Thr Tyr
            20                  25                  30

Val Val Leu Asp Trp Asn Tyr Arg Trp Ile His Asp Ala Asn Tyr Asn
        35                  40                  45

Ser Cys Thr Val Asn Gly Gly Val Asn Thr Thr Leu Cys Pro Asp Glu
    50                  55                  60

```
Ala Thr Gly Ser Lys Asn Cys Phe Ile Glu Gly Val Asp Tyr Ala Ala
 65                  70                  75                  80

Ser Gly Val Thr Ala Asn Gly Ser Thr Leu Thr Leu Asn Gln Tyr Met
                 85                  90                  95

Pro Ser Ser Gly Gly Tyr Thr Ser Val Ser Pro Arg Leu Tyr Leu
            100                 105                 110

Leu Gly Pro Asp Gly Lys Tyr Val Met Leu Lys Leu Asn Gly Gln Glu
            115                 120                 125

Leu Ser Phe Asp Val Asp Leu Ser Ala Leu Pro Cys Gly Glu Asn Ala
            130                 135                 140

Ser Leu Tyr Leu Ser Gln Met Asp Glu Asn Gly Gly Ala Asn Gln Tyr
145                 150                 155                 160

Asn Thr Ala Gly Ala Asn Tyr Gly Ser Gly Tyr Cys Asp Ala Gln Cys
                165                 170                 175

Pro Val Gln Thr Trp Arg Asn Gly Thr Leu Asn Thr Ser Gly Gln Gly
            180                 185                 190

Phe Cys Cys Asn Glu Met Asp Ile Leu Glu Gly Asn Ser Arg Ala Asn
            195                 200                 205

Ala Leu Thr Pro His Ser Cys Asn Ala Thr Ala Cys Asp Ser Ala Gly
            210                 215                 220

Cys Gly Phe Asn Pro Tyr Arg Ser Gly Tyr Pro Asn Tyr Phe Gly Pro
225                 230                 235                 240

Gly Gly Thr Val Asp Thr Ser Lys Pro Phe Thr Ile Ile Thr Gln Phe
                245                 250                 255

Asn Thr Asp Asn Gly Ser Pro Ser Gly Asn Leu Val Ser Ile Thr Arg
                260                 265                 270

Lys Tyr Arg Gln Asn Gly Val Asp Ile Pro Ser Ala Lys Pro Gly Gly
            275                 280                 285

Asp Thr Ile Ser Ser Cys Pro Ser Ala Ser Thr Tyr Gly Gly Leu Ala
            290                 295                 300

Thr Met Gly Lys Ala Leu Ser Glu Gly Met Val Leu Ile Phe Ser Ile
305                 310                 315                 320

Trp Asn Asp Asn Ser Gln Tyr Met Asn Trp Leu Asp Ser Gly Asp Ala
                325                 330                 335

Gly Pro Cys Ser Ser Thr Glu Gly Asn Pro Ser Asn Ile Leu Ala Asn
            340                 345                 350

Asn Pro Gly Thr His Val Val Tyr Ser Asn Ile Arg Trp Gly Asp Ile
            355                 360                 365

Gly Ser Thr Thr Asn Ser Thr Gly Gly Asn Pro Pro Pro Pro Ala
            370                 375                 380

Ser Ser Thr Thr Phe Ser Thr Ala Arg Arg Ser Ser Thr Ser Ser Ser
385                 390                 395                 400

Ser Pro Ser Cys Ile Gln Thr His Trp Gly Gln Cys Gly Gly Ile Gly
                405                 410                 415

Tyr Thr Gly Cys Lys Thr Cys Thr Ser Gly Thr Thr Cys Gln Tyr Ser
            420                 425                 430

Asn Asp Tyr Tyr Ser Gln Cys Leu
            435                 440

<210> SEQ ID NO 3
<211> LENGTH: 1323
<212> TYPE: DNA
<213> ORGANISM: Hypocrea pseudokonigii
```

<400> SEQUENCE: 3

```
tctcagcagc caggaacttc tactccagag gtgcacccaa agctgaccac ctacaagtgt      60
accacctctg gtggttgtgt tgctcaggac acctctgttg ttctggactg gaactacaga    120
tggatgcacg acgccaacta caactcttgt accgtgaacg gtggtgtcaa cactactctg    180
tgtccagacg aggctacttg tggcaagaac tgcttcatcg agggtgttga ctacgctgct    240
tctggtgtta ctgcctctgg ttctaccttg accctgaacc agtacatgcc atcttcctct    300
ggcggttact cttctgtgtc gccaagactg tacttgttgg gtccagacgg tgagtacgtt    360
atgctgaagc tgaacggaca ggagctgtct tttgacgttg acctgtctgc tttgccatgt    420
ggagagaacg gttctctgta cctgtctcag atggacgaga acggtggagc taaccagtac    480
aacaccgccg gtgctaacta cggttctggt tactgtgacg cccagtgtcc agttcagact    540
tggagaaacg gaaccctgaa cacttctggc cagggattct gctgtaacga gatggacatc    600
ttggagggaa actctagagc taacgctctg accccacact cttgtactgc taccgcttgt    660
gactctgctg gttgcggttt taacccatac ggctcgggtt acccaaacta ctttggccca    720
ggtgacactg ttgacacctc gaagccattc accatcatca cccagttcaa caccgacaac    780
ggttctccat ctggtaacct ggtgtcgatc accagaaagt acagacagaa cggcgttgac    840
atcccatctg ctaaaccagg tggcgacacc atttcgtctt gtccatctgc ctctgcttac    900
ggtggattgg ctaccatggg aaaggctctg tcctctggaa tggtgctgat cttctcgatc    960
tggaacgaca actcgcagta catgaactgg ctggactctg ttctgctggg tccatgttct   1020
tctaccgagg caacccatc taacatcctg gctaacaacc tggtactca cgtggtgtac   1080
tcgaacatta gatggggcga cattggttct accaccaact ctaccggtgg taacccacca   1140
ccaccacctg catcttctac caccttctcg accaccagaa gatcgtctac cacctcttct   1200
tctccatctt gtacccagac tcactggggt cagtgtggtg gtattggcta caccggctgt   1260
aagacctgta cctctggaac cacttgccag tacggcaacg actactactc tcagtgcctg   1320
tga                                                                 1323
```

<210> SEQ ID NO 4
<211> LENGTH: 440
<212> TYPE: PRT
<213> ORGANISM: Hypocrea pseudokonigii

<400> SEQUENCE: 4

```
Ser Gln Gln Pro Gly Thr Ser Thr Pro Glu Val His Pro Lys Leu Thr
1               5                  10                  15

Thr Tyr Lys Cys Thr Thr Ser Gly Gly Cys Val Ala Gln Asp Thr Ser
            20                  25                  30

Val Val Leu Asp Trp Asn Tyr Arg Trp Met His Asp Ala Asn Tyr Asn
        35                  40                  45

Ser Cys Thr Val Asn Gly Gly Val Asn Thr Thr Leu Cys Pro Asp Glu
    50                  55                  60

Ala Thr Cys Gly Lys Asn Cys Phe Ile Glu Gly Val Asp Tyr Ala Ala
65                  70                  75                  80

Ser Gly Val Thr Ala Ser Gly Ser Thr Leu Thr Leu Asn Gln Tyr Met
                85                  90                  95

Pro Ser Ser Ser Gly Gly Tyr Ser Ser Val Ser Pro Arg Leu Tyr Leu
            100                 105                 110

Leu Gly Pro Asp Gly Glu Tyr Val Met Leu Lys Leu Asn Gly Gln Glu
        115                 120                 125
```

-continued

```
Leu Ser Phe Asp Val Asp Leu Ser Ala Leu Pro Cys Gly Glu Asn Gly
        130                 135                 140

Ser Leu Tyr Leu Ser Gln Met Asp Glu Asn Gly Ala Asn Gln Tyr
145                 150                 155                 160

Asn Thr Ala Gly Ala Asn Tyr Gly Ser Gly Tyr Cys Asp Ala Gln Cys
                165                 170                 175

Pro Val Gln Thr Trp Arg Asn Gly Thr Leu Asn Thr Ser Gly Gln Gly
            180                 185                 190

Phe Cys Cys Asn Glu Met Asp Ile Leu Glu Gly Asn Ser Arg Ala Asn
        195                 200                 205

Ala Leu Thr Pro His Ser Cys Thr Ala Thr Ala Cys Asp Ser Ala Gly
    210                 215                 220

Cys Gly Phe Asn Pro Tyr Gly Ser Gly Tyr Pro Asn Tyr Phe Gly Pro
225                 230                 235                 240

Gly Asp Thr Val Asp Thr Ser Lys Pro Phe Thr Ile Ile Thr Gln Phe
                245                 250                 255

Asn Thr Asp Asn Gly Ser Pro Ser Gly Asn Leu Val Ser Ile Thr Arg
            260                 265                 270

Lys Tyr Arg Gln Asn Gly Val Asp Ile Pro Ser Ala Lys Pro Gly Gly
        275                 280                 285

Asp Thr Ile Ser Ser Cys Pro Ser Ala Ser Ala Tyr Gly Gly Leu Ala
    290                 295                 300

Thr Met Gly Lys Ala Leu Ser Ser Gly Met Val Leu Ile Phe Ser Ile
305                 310                 315                 320

Trp Asn Asp Asn Ser Gln Tyr Met Asn Trp Leu Asp Ser Gly Ser Ala
                325                 330                 335

Gly Pro Cys Ser Ser Thr Glu Gly Asn Pro Ser Asn Ile Leu Ala Asn
            340                 345                 350

Asn Pro Gly Thr His Val Val Tyr Ser Asn Ile Arg Trp Gly Asp Ile
        355                 360                 365

Gly Ser Thr Thr Asn Ser Thr Gly Gly Asn Pro Pro Pro Pro Ala
    370                 375                 380

Ser Ser Thr Thr Phe Ser Thr Thr Arg Arg Ser Ser Thr Thr Ser Ser
385                 390                 395                 400

Ser Pro Ser Cys Thr Gln Thr His Trp Gly Gln Cys Gly Gly Ile Gly
                405                 410                 415

Tyr Thr Gly Cys Lys Thr Cys Thr Ser Gly Thr Thr Cys Gln Tyr Gly
            420                 425                 430

Asn Asp Tyr Tyr Ser Gln Cys Leu
        435                 440

<210> SEQ ID NO 5
<211> LENGTH: 440
<212> TYPE: PRT
<213> ORGANISM: artificial
<220> FEATURE:
<223> OTHER INFORMATION: artificial construct

<400> SEQUENCE: 5

Ser Gln Gln Pro Gly Thr Ser Pro Glu Val His Pro Lys Leu Thr
1               5                   10                  15

Thr Tyr Lys Cys Thr Thr Ser Gly Gly Cys Val Ala Gln Asp Thr Ser
                20                  25                  30

Val Val Leu Asp Trp Asn Tyr Arg Trp Met His Asp Ala Asn Tyr Asn
            35                  40                  45
```

```
Ser Cys Thr Val Asn Gly Gly Val Asn Thr Thr Leu Cys Pro Asp Glu
 50                  55                  60

Ala Thr Cys Gly Lys Asn Cys Phe Ile Glu Gly Val Asp Tyr Ala Ala
 65                  70                  75                  80

Ser Gly Val Thr Ala Ser Gly Ser Thr Leu Thr Leu Asn Gln Tyr Met
                     85                  90                  95

Pro Ser Ser Ser Gly Gly Tyr Ser Ser Val Ser Pro Arg Leu Tyr Leu
                100                 105                 110

Leu Gly Pro Asp Gly Glu Tyr Val Met Leu Lys Leu Asn Gly Gln Glu
            115                 120                 125

Leu Ser Phe Asp Val Asp Leu Ser Ala Leu Pro Cys Gly Glu Asn Gly
            130                 135                 140

Ser Leu Tyr Leu Ser Gln Met Asp Lys Asn Gly Gly Ala Asn Gln Tyr
145                 150                 155                 160

Asn Thr Ala Gly Ala Asn Tyr Gly Ser Gly Tyr Cys Asp Ala Gln Cys
                165                 170                 175

Pro Val Gln Thr Trp Arg Asn Gly Thr Leu Asn Thr Ser Gly Gln Gly
                180                 185                 190

Phe Cys Cys Asn Glu Met Asp Ile Leu Glu Gly Asn Ser Arg Ala Asn
                195                 200                 205

Ala Leu Thr Pro His Ser Cys Thr Ala Thr Ala Cys Asp Ser Ala Gly
            210                 215                 220

Cys Gly Phe Asn Pro Tyr Gly Ser Gly Tyr Pro Asn Tyr Phe Gly Pro
225                 230                 235                 240

Gly Asp Thr Val Asp Thr Ser Lys Pro Phe Thr Ile Ile Thr Gln Phe
                245                 250                 255

Asn Thr Asp Asn Gly Ser Pro Ser Gly Asn Leu Val Ser Ile Thr Arg
                260                 265                 270

Lys Tyr Arg Gln Asn Gly Val Asp Ile Pro Ser Ala Lys Pro Gly Gly
            275                 280                 285

Asp Thr Ile Ser Ser Cys Pro Ser Ala Ser Ala Tyr Gly Gly Leu Ala
            290                 295                 300

Thr Met Gly Lys Ala Leu Ser Ser Gly Met Val Leu Ile Phe Ser Ile
305                 310                 315                 320

Trp Asn Asp Asn Ser Gln Tyr Met Asn Trp Leu Asp Ser Gly Ser Ala
                325                 330                 335

Gly Pro Cys Ser Ser Thr Glu Gly Asn Pro Ser Asn Ile Leu Ala Asn
                340                 345                 350

Asn Pro Gly Thr His Val Val Tyr Ser Asn Ile Arg Trp Gly Asp Ile
            355                 360                 365

Gly Ser Thr Thr Asn Ser Thr Gly Gly Asn Pro Pro Pro Pro Pro Ala
            370                 375                 380

Ser Ser Thr Thr Phe Ser Thr Thr Arg Arg Ser Ser Thr Thr Ser Ser
385                 390                 395                 400

Ser Pro Ser Cys Thr Gln Thr His Trp Gly Gln Cys Gly Gly Ile Gly
                405                 410                 415

Tyr Thr Gly Cys Lys Thr Cys Thr Ser Gly Thr Thr Cys Gln Tyr Gly
                420                 425                 430

Asn Asp Tyr Tyr Ser Gln Cys Leu
            435                 440

<210> SEQ ID NO 6
<211> LENGTH: 440
```

```
<212> TYPE: PRT
<213> ORGANISM: artificial
<220> FEATURE:
<223> OTHER INFORMATION: artificial construct

<400> SEQUENCE: 6
```

| | | | | | | | | | | | | | | |
|---|---|---|---|---|---|---|---|---|---|---|---|---|---|---|
| Ser | Leu | Gln | Pro | Gly | Thr | Ser | Thr | Pro | Glu | Val | His | Pro | Lys | Leu | Thr |
| 1 | | | | 5 | | | | | 10 | | | | | 15 |

| Thr | Tyr | Lys | Cys | Thr | Thr | Ser | Gly | Gly | Cys | Val | Ala | Gln | Asn | Thr | Ser |
| | | | 20 | | | | | 25 | | | | | 30 | | |

| Val | Val | Leu | Asp | Trp | Asn | Tyr | Arg | Trp | Met | His | Asp | Ala | Asn | Tyr | Asn |
| | | | 35 | | | | 40 | | | | | 45 | | | |

| Ser | Cys | Thr | Val | Asn | Gly | Gly | Val | Asn | Thr | Thr | Leu | Cys | Pro | Asp | Glu |
| | 50 | | | | | 55 | | | | | 60 | | | | |

| Ala | Thr | Gly | Gly | Lys | Asn | Cys | Phe | Ile | Glu | Gly | Val | Asp | Tyr | Ala | Ala |
| 65 | | | | | 70 | | | | | 75 | | | | | 80 |

| Ser | Gly | Val | Thr | Ala | Ser | Gly | Ser | Thr | Leu | Thr | Leu | Asn | Gln | Tyr | Met |
| | | | | 85 | | | | | 90 | | | | | 95 | |

| Pro | Ser | Ser | Ser | Gly | Gly | Tyr | Ser | Ser | Val | Ser | Pro | Arg | Leu | Tyr | Leu |
| | | | 100 | | | | | 105 | | | | | 110 | | |

| Leu | Gly | Pro | Asp | Gly | Lys | Tyr | Val | Met | Leu | Lys | Leu | Asn | Gly | Gln | Glu |
| | | | | 115 | | | | | 120 | | | | | 125 | |

| Leu | Ser | Phe | Asp | Val | Asp | Leu | Ser | Ala | Leu | Pro | Cys | Gly | Glu | Asn | Ala |
| | 130 | | | | | 135 | | | | | 140 | | | | |

| Ser | Leu | Tyr | Leu | Ser | Gln | Met | Asp | Glu | Asn | Gly | Gly | Ala | Asn | Gln | Tyr |
| 145 | | | | | 150 | | | | | 155 | | | | | 160 |

| Asn | Thr | Ala | Gly | Ala | Asn | Tyr | Gly | Ser | Gly | Tyr | Cys | Asp | Ala | Gln | Cys |
| | | | | 165 | | | | | 170 | | | | | 175 | |

| Pro | Val | Gln | Thr | Trp | Arg | Asn | Gly | Thr | Leu | Asn | Thr | Ser | Gly | Gln | Gly |
| | | | 180 | | | | | 185 | | | | | 190 | | |

| Phe | Cys | Cys | Asn | Glu | Met | Asp | Ile | Leu | Glu | Gly | Asn | Ser | Arg | Ala | Asn |
| | | | 195 | | | | | 200 | | | | | 205 | | |

| Ala | Leu | Thr | Pro | His | Ser | Cys | Asn | Ala | Thr | Ala | Cys | Asp | Ser | Ala | Gly |
| | 210 | | | | | 215 | | | | | 220 | | | | |

| Cys | Gly | Phe | Asn | Pro | Tyr | Gly | Ser | Gly | Tyr | Pro | Asn | Tyr | Phe | Gly | Pro |
| 225 | | | | | 230 | | | | | 235 | | | | | 240 |

| Gly | Gly | Thr | Val | Asp | Thr | Ser | Lys | Pro | Phe | Thr | Ile | Ile | Thr | Gln | Phe |
| | | | | 245 | | | | | 250 | | | | | 255 | |

| Asn | Thr | Asp | Asn | Gly | Ser | Pro | Ser | Gly | Asn | Leu | Val | Ser | Ile | Thr | Arg |
| | | | 260 | | | | | 265 | | | | | 270 | | |

| Lys | Tyr | Arg | Gln | Asn | Gly | Val | Asp | Ile | Pro | Ser | Ala | Lys | Pro | Gly | Gly |
| | | 275 | | | | | 280 | | | | | 285 | | | |

| Asp | Thr | Ile | Ser | Ser | Cys | Pro | Ser | Ala | Ser | Thr | Tyr | Gly | Gly | Leu | Ala |
| | 290 | | | | | 295 | | | | | 300 | | | | |

| Thr | Met | Gly | Lys | Ala | Leu | Ser | Ser | Gly | Met | Val | Leu | Ile | Phe | Ser | Ile |
| 305 | | | | | 310 | | | | | 315 | | | | | 320 |

| Trp | Asn | Asp | Asn | Ser | Gln | Tyr | Met | Asn | Trp | Leu | Asp | Ser | Gly | Ser | Ala |
| | | | | 325 | | | | | 330 | | | | | 335 | |

| Gly | Pro | Cys | Ser | Ser | Thr | Glu | Gly | Asn | Pro | Ser | Asn | Ile | Leu | Ala | Asn |
| | | | 340 | | | | | 345 | | | | | 350 | | |

| Asn | Pro | Gly | Thr | His | Val | Val | Tyr | Ser | Asn | Ile | Arg | Trp | Gly | Asp | Ile |
| | | 355 | | | | | 360 | | | | | 365 | | | |

| Gly | Ser | Thr | Thr | Asn | Ser | Thr | Gly | Gly | Asn | Pro | Pro | Pro | Pro | Ala | |
| | 370 | | | | | 375 | | | | | 380 | | | | |

```
Ser Ser Thr Thr Phe Ser Thr Thr Arg Arg Ser Ser Thr Ser Ser Ser
385                 390                 395                 400

Ser Pro Ser Cys Ile Gln Thr His Trp Gly Gln Cys Gly Gly Ile Gly
            405                 410                 415

Tyr Thr Gly Cys Lys Thr Cys Thr Ser Gly Thr Thr Cys Gln Tyr Ser
            420                 425                 430

Asn Asp Tyr Tyr Ser Gln Cys Leu
        435                 440

<210> SEQ ID NO 7
<211> LENGTH: 440
<212> TYPE: PRT
<213> ORGANISM: artificial
<220> FEATURE:
<223> OTHER INFORMATION: artificial construct

<400> SEQUENCE: 7

Ser Leu Gln Pro Gly Thr Ser Thr Pro Glu Val His Pro Lys Leu Thr
1               5                   10                  15

Thr Tyr Lys Cys Thr Thr Ser Gly Gly Cys Val Ala Gln Asn Thr Tyr
                20                  25                  30

Val Val Leu Asp Trp Asn Tyr Arg Trp Ile His Asp Ala Asn Tyr Asn
            35                  40                  45

Ser Cys Thr Val Asn Gly Gly Val Asn Thr Thr Leu Cys Pro Asp Glu
    50                  55                  60

Ala Thr Gly Ser Lys Asn Cys Phe Ile Glu Gly Val Asp Tyr Ala Ala
65                  70                  75                  80

Ser Gly Val Thr Ala Asn Gly Ser Thr Leu Thr Leu Asn Gln Tyr Met
                85                  90                  95

Pro Ser Ser Ser Gly Gly Tyr Thr Ser Val Ser Pro Arg Leu Tyr Leu
                100                 105                 110

Leu Gly Pro Asp Gly Lys Tyr Val Met Leu Lys Leu Asn Gly Gln Glu
            115                 120                 125

Leu Ser Phe Asp Val Asp Leu Ser Ala Leu Pro Cys Gly Glu Asn Ala
    130                 135                 140

Ser Leu Tyr Leu Ser Gln Met Asp Glu Asn Gly Gly Ala Asn Gln Tyr
145                 150                 155                 160

Asn Thr Ala Gly Ala Asn Tyr Gly Ser Gly Tyr Cys Asp Ala Gln Cys
                165                 170                 175

Pro Val Gln Thr Trp Arg Asn Gly Thr Leu Asn Thr Ser Gly Gln Gly
            180                 185                 190

Phe Cys Cys Asn Glu Met Asp Ile Leu Glu Gly Asn Ser Arg Ala Asn
    195                 200                 205

Ala Leu Thr Pro His Ser Cys Asn Ala Thr Ala Cys Asp Ser Ala Gly
210                 215                 220

Cys Gly Phe Asn Pro Tyr Gly Ser Gly Tyr Pro Asn Tyr Phe Gly Pro
225                 230                 235                 240

Gly Gly Thr Val Asp Thr Ser Lys Pro Phe Thr Ile Ile Thr Gln Phe
                245                 250                 255

Asn Thr Asp Asn Gly Ser Pro Ser Gly Asn Leu Val Ser Ile Thr Arg
            260                 265                 270

Lys Tyr Arg Gln Asn Gly Val Asp Ile Pro Ser Ala Lys Pro Gly Gly
    275                 280                 285

Asp Thr Ile Ser Ser Cys Pro Ser Ala Ser Thr Tyr Gly Gly Leu Ala
290                 295                 300
```

```
Thr Met Gly Lys Ala Leu Ser Ser Gly Met Val Leu Ile Phe Ser Ile
305                 310                 315                 320

Trp Asn Asp Asn Ser Gln Tyr Met Asn Trp Leu Asp Ser Gly Ser Ala
            325                 330                 335

Gly Pro Cys Ser Ser Thr Glu Gly Asn Pro Ser Asn Ile Leu Ala Asn
            340                 345                 350

Asn Pro Gly Thr His Val Val Tyr Ser Asn Ile Arg Trp Gly Asp Ile
            355                 360                 365

Gly Ser Thr Thr Asn Ser Thr Gly Gly Asn Pro Pro Pro Pro Pro Ala
            370                 375                 380

Ser Ser Thr Thr Phe Ser Thr Thr Arg Arg Ser Ser Thr Ser Ser Ser
385                 390                 395                 400

Ser Pro Ser Cys Ile Gln Thr His Trp Gly Gln Cys Gly Gly Ile Gly
            405                 410                 415

Tyr Thr Gly Cys Lys Thr Cys Thr Ser Gly Thr Thr Cys Gln Tyr Ser
            420                 425                 430

Asn Asp Tyr Tyr Ser Gln Cys Leu
            435                 440

<210> SEQ ID NO 8
<211> LENGTH: 440
<212> TYPE: PRT
<213> ORGANISM: artificial
<220> FEATURE:
<223> OTHER INFORMATION: artificial construct

<400> SEQUENCE: 8

Ser Gln Gln Pro Gly Thr Ser Thr Pro Glu Val His Pro Lys Leu Thr
1               5                   10                  15

Thr Tyr Lys Cys Thr Thr Ser Gly Gly Cys Val Ala Gln Asn Thr Ser
            20                  25                  30

Val Val Leu Asp Trp Asn Tyr Arg Trp Met His Asp Ala Asn Tyr Asn
            35                  40                  45

Ser Cys Thr Val Asn Gly Gly Val Asn Thr Thr Leu Cys Pro Asp Glu
50                  55                  60

Ala Thr Cys Gly Lys Asn Cys Phe Ile Glu Gly Val Asp Tyr Ala Ala
65                  70                  75                  80

Ser Gly Val Thr Ala Ser Gly Ser Thr Leu Thr Leu Asn Gln Tyr Met
            85                  90                  95

Pro Ser Ser Ser Gly Gly Tyr Ser Ser Val Ser Pro Arg Leu Tyr Leu
            100                 105                 110

Leu Gly Pro Asp Gly Lys Tyr Val Met Leu Lys Leu Asn Gly Gln Glu
            115                 120                 125

Leu Ser Phe Asp Val Asp Leu Ser Ala Leu Pro Cys Gly Glu Asn Ala
130                 135                 140

Ser Leu Tyr Leu Ser Gln Met Asp Glu Asn Gly Gly Ala Asn Gln Tyr
145                 150                 155                 160

Asn Thr Ala Gly Ala Asn Tyr Gly Ser Gly Tyr Cys Asp Ala Gln Cys
            165                 170                 175

Pro Val Gln Thr Trp Arg Asn Gly Thr Leu Asn Thr Ser Gly Gln Gly
            180                 185                 190

Phe Cys Cys Asn Glu Met Asp Ile Leu Glu Gly Asn Ser Arg Ala Asn
            195                 200                 205

Ala Leu Thr Pro His Ser Cys Asn Ala Thr Ala Cys Asp Ser Ala Gly
            210                 215                 220
```

-continued

```
Cys Gly Phe Asn Pro Tyr Gly Ser Gly Tyr Pro Asn Tyr Phe Gly Pro
225                 230                 235                 240

Gly Gly Thr Val Asp Thr Ser Lys Pro Phe Thr Ile Ile Thr Gln Phe
            245                 250                 255

Asn Thr Asp Asn Gly Ser Pro Ser Gly Asn Leu Val Ser Ile Thr Arg
            260                 265                 270

Lys Tyr Arg Gln Asn Gly Val Asp Ile Pro Ser Ala Lys Pro Gly Gly
        275                 280                 285

Asp Thr Ile Ser Ser Cys Pro Ser Ala Ser Ala Tyr Gly Gly Leu Ala
    290                 295                 300

Thr Met Gly Lys Ala Leu Ser Ser Gly Met Val Leu Ile Phe Ser Ile
305                 310                 315                 320

Trp Asn Asp Asn Ser Gln Tyr Met Asn Trp Leu Asp Ser Gly Ser Ala
                325                 330                 335

Gly Pro Cys Ser Ser Thr Glu Gly Asn Pro Ser Asn Ile Leu Ala Asn
            340                 345                 350

Asn Pro Gly Thr His Val Val Tyr Ser Asn Ile Arg Trp Gly Asp Ile
        355                 360                 365

Gly Ser Thr Thr Asn Ser Thr Gly Gly Asn Pro Pro Pro Pro Pro Ala
370                 375                 380

Ser Ser Thr Thr Phe Ser Thr Thr Arg Arg Ser Ser Thr Thr Ser Ser
385                 390                 395                 400

Ser Pro Ser Cys Thr Gln Thr His Trp Gly Gln Cys Gly Gly Ile Gly
                405                 410                 415

Tyr Thr Gly Cys Lys Thr Cys Thr Ser Gly Thr Thr Cys Gln Tyr Gly
            420                 425                 430

Asn Asp Tyr Tyr Ser Gln Cys Leu
        435                 440

<210> SEQ ID NO 9
<211> LENGTH: 440
<212> TYPE: PRT
<213> ORGANISM: artificial
<220> FEATURE:
<223> OTHER INFORMATION: artificial construct

<400> SEQUENCE: 9

Ser Leu Gln Pro Gly Thr Ser Thr Pro Glu Val His Pro Lys Leu Thr
1               5                   10                  15

Thr Tyr Lys Cys Thr Thr Ser Gly Gly Cys Val Ala Gln Asn Thr Ser
            20                  25                  30

Val Val Leu Asp Trp Asn Tyr Arg Trp Met His Asp Ala Asn Tyr Asn
        35                  40                  45

Ser Cys Thr Val Asn Gly Gly Val Asn Thr Thr Leu Cys Pro Asp Glu
    50                  55                  60

Ala Thr Cys Cys Lys Asn Cys Phe Ile Glu Gly Val Asp Tyr Ala Ala
65                  70                  75                  80

Ser Gly Val Thr Ala Ser Gly Ser Thr Leu Thr Leu Asn Gln Tyr Met
                85                  90                  95

Pro Ser Ser Ser Gly Gly Tyr Ser Ser Val Ser Pro Arg Leu Tyr Leu
            100                 105                 110

Leu Gly Pro Asp Gly Lys Tyr Val Met Leu Lys Leu Asn Gly Gln Glu
        115                 120                 125

Leu Ser Phe Asp Val Asp Leu Ser Ala Leu Pro Cys Gly Glu Asn Ala
    130                 135                 140
```

Ser Leu Tyr Leu Ser Gln Met Asp Glu Asn Gly Gly Ala Asn Gln Tyr
145                 150                 155                 160

Asn Thr Ala Gly Ala Asn Tyr Gly Ser Gly Tyr Cys Asp Ala Gln Cys
            165                 170                 175

Pro Val Gln Thr Trp Arg Asn Gly Thr Leu Asn Thr Ser Gly Lys Gly
            180                 185                 190

Phe Cys Cys Asn Glu Met Asp Ile Leu Glu Gly Asn Ser Arg Ala Asn
        195                 200                 205

Ala Leu Thr Pro His Ser Cys Asn Ala Thr Ala Cys Asp Ser Ala Gly
        210                 215                 220

Cys Gly Phe Asn Pro Tyr Gly Ser Gly Tyr Pro Asn Tyr Phe Gly Pro
225                 230                 235                 240

Gly Gly Thr Val Asp Thr Ser Lys Pro Phe Thr Ile Ile Thr Gln Phe
            245                 250                 255

Asn Thr Asp Asn Gly Ser Pro Ser Gly Asn Leu Val Ser Ile Thr Arg
            260                 265                 270

Lys Tyr Arg Gln Asn Gly Val Asp Ile Pro Ser Ala Lys Pro Gly Gly
        275                 280                 285

Asp Thr Ile Ser Ser Cys Pro Ser Ala Ser Ala Tyr Gly Gly Leu Ala
        290                 295                 300

Thr Met Gly Lys Ala Leu Ser Ser Gly Met Val Leu Ile Phe Ser Ile
305                 310                 315                 320

Trp Asn Asp Asn Ser Gln Tyr Met Asn Trp Leu Asp Ser Gly Ser Ala
            325                 330                 335

Gly Pro Cys Ser Ser Thr Glu Gly Asn Pro Ser Asn Ile Leu Ala Asn
            340                 345                 350

Asn Pro Gly Thr His Val Val Tyr Ser Asn Ile Arg Trp Gly Asp Ile
            355                 360                 365

Gly Ser Thr Thr Asn Ser Thr Gly Gly Asn Pro Pro Pro Pro Pro Ala
        370                 375                 380

Ser Ser Thr Thr Phe Ser Thr Thr Arg Arg Ser Ser Thr Thr Ser Ser
385                 390                 395                 400

Ser Pro Ser Cys Thr Gln Thr His Trp Gly Gln Cys Gly Gly Ile Gly
            405                 410                 415

Tyr Thr Gly Cys Lys Thr Cys Thr Ser Gly Thr Thr Cys Gln Tyr Ser
            420                 425                 430

Asn Asp Tyr Tyr Ser Gln Cys Leu
        435                 440

<210> SEQ ID NO 10
<211> LENGTH: 440
<212> TYPE: PRT
<213> ORGANISM: artificial
<220> FEATURE:
<223> OTHER INFORMATION: artificial construct

<400> SEQUENCE: 10

Ser Gln Gln Pro Gly Thr Ser Thr Pro Glu Val His Pro Lys Leu Thr
1               5                   10                  15

Thr Tyr Lys Cys Thr Thr Ser Gly Gly Cys Val Ala Gln Asn Thr Ser
            20                  25                  30

Val Val Leu Asp Trp Asn Tyr Arg Trp Met His Asp Ala Asn Tyr Asn
        35                  40                  45

Ser Cys Thr Val Asn Gly Gly Val Asn Thr Thr Leu Cys Pro Asp Glu
    50                  55                  60

```
Ala Thr Cys Gly Lys Asn Cys Phe Ile Glu Gly Val Asp Tyr Ala Ala
 65                  70                  75                  80

Ser Gly Val Thr Ala Ser Gly Ser Thr Leu Thr Leu Asn Gln Tyr Met
             85                      90                  95

Pro Ser Ser Ser Gly Gly Tyr Ser Ser Val Ser Pro Arg Leu Tyr Leu
            100                 105                 110

Leu Gly Pro Asp Gly Lys Tyr Val Met Leu Lys Leu Asn Gly Gln Glu
        115                 120                 125

Leu Ser Phe Asp Val Asp Leu Ser Ala Leu Pro Cys Gly Glu Asn Ala
    130                 135                 140

Ser Leu Tyr Leu Ser Gln Met Asp Glu Asn Gly Gly Ala Asn Gln Tyr
145                 150                 155                 160

Asn Thr Ala Gly Ala Asn Tyr Gly Ser Gly Tyr Cys Asp Ala Gln Cys
                165                 170                 175

Pro Val Gln Thr Trp Arg Asn Gly Thr Leu Asn Thr Ser Gly Gln Gly
            180                 185                 190

Phe Cys Cys Asn Glu Met Asp Ile Leu Glu Gly Asn Ser Arg Ala Asn
        195                 200                 205

Ala Leu Thr Pro His Ser Cys Asn Ala Thr Ala Cys Asp Ser Ala Gly
    210                 215                 220

Cys Gly Phe Asn Pro Tyr Lys Ser Gly Tyr Pro Asn Tyr Phe Gly Pro
225                 230                 235                 240

Gly Gly Thr Val Asp Thr Ser Lys Pro Phe Thr Ile Ile Thr Gln Phe
                245                 250                 255

Asn Thr Asp Asn Gly Ser Pro Ser Gly Asn Leu Val Ser Ile Thr Arg
            260                 265                 270

Lys Tyr Arg Gln Asn Gly Val Asp Ile Pro Ser Ala Lys Pro Gly Gly
        275                 280                 285

Asp Thr Ile Ser Ser Cys Pro Ser Ala Ser Ala Tyr Gly Gly Leu Ala
    290                 295                 300

Thr Met Gly Lys Ala Leu Ser Glu Gly Met Val Leu Ile Phe Ser Ile
305                 310                 315                 320

Trp Asn Asp Asn Ser Gln Tyr Met Asn Trp Leu Asp Ser Gly Ser Ala
                325                 330                 335

Gly Pro Cys Ser Ser Thr Glu Gly Asn Pro Ser Asn Ile Leu Ala Asn
            340                 345                 350

Asn Pro Gly Thr His Val Val Tyr Ser Asn Ile Arg Trp Gly Asp Ile
        355                 360                 365

Gly Ser Thr Thr Asn Ser Thr Gly Gly Asn Pro Pro Pro Pro Pro Ala
    370                 375                 380

Ser Ser Thr Thr Phe Ser Thr Thr Arg Arg Ser Ser Thr Thr Ser Ser
385                 390                 395                 400

Ser Pro Ser Cys Thr Gln Thr His Trp Gly Gln Cys Gly Gly Ile Gly
                405                 410                 415

Tyr Thr Gly Cys Lys Thr Cys Thr Ser Gly Thr Thr Cys Gln Tyr Gly
            420                 425                 430

Asn Asp Tyr Tyr Ser Gln Cys Leu
        435                 440

<210> SEQ ID NO 11
<211> LENGTH: 440
<212> TYPE: PRT
<213> ORGANISM: artificial
<220> FEATURE:
<223> OTHER INFORMATION: artificial construct
```

```
<400> SEQUENCE: 11

Ser Gln Gln Pro Gly Thr Ser Thr Pro Glu Val His Pro Lys Leu Thr
1               5                   10                  15

Thr Tyr Lys Cys Thr Thr Ser Gly Gly Cys Val Ala Gln Asn Thr Ser
            20                  25                  30

Val Val Leu Asp Trp Asn Tyr Arg Trp Met His Asp Ala Asn Tyr Asn
        35                  40                  45

Ser Cys Thr Val Asn Gly Val Asn Thr Thr Leu Cys Pro Asp Glu
50                  55                  60

Ala Thr Cys Gly Lys Asn Cys Phe Ile Glu Gly Val Asp Tyr Ala Ala
65                  70                  75                  80

Ser Gly Val Thr Ala Ser Gly Ser Thr Leu Thr Leu Asn Gln Tyr Met
                85                  90                  95

Pro Ser Ser Ser Gly Gly Tyr Ser Ser Val Ser Pro Arg Leu Tyr Leu
                100                 105                 110

Leu Gly Pro Asp Gly Lys Tyr Val Met Leu Lys Leu Asn Gly Gln Glu
            115                 120                 125

Leu Ser Phe Asp Val Asp Leu Ser Ala Leu Pro Cys Gly Glu Asn Ala
130                 135                 140

Ser Leu Tyr Leu Ser Gln Met Asp Glu Asn Gly Gly Ala Asn Gln Tyr
145                 150                 155                 160

Asn Thr Ala Gly Ala Asn Tyr Gly Ser Gly Tyr Cys Asp Ala Gln Cys
                165                 170                 175

Pro Val Gln Thr Trp Arg Asn Gly Thr Leu Asn Thr Ser Gly Gln Gly
            180                 185                 190

Phe Cys Cys Asn Glu Met Asp Ile Leu Glu Gly Asn Ser Arg Ala Asn
        195                 200                 205

Ala Leu Thr Pro His Ser Cys Asn Ala Thr Ala Cys Asp Ser Ala Gly
210                 215                 220

Cys Gly Phe Asn Pro Tyr Gly Ser Gly Tyr Pro Asn Tyr Phe Gly Pro
225                 230                 235                 240

Gly Gly Thr Val Asp Thr Ser Lys Pro Phe Thr Ile Ile Thr Gln Phe
                245                 250                 255

Asn Thr Asp Asn Gly Ser Pro Ser Gly Asn Leu Val Ser Ile Thr Arg
            260                 265                 270

Lys Tyr Arg Gln Asn Gly Val Asp Ile Pro Ser Ala Lys Pro Gly Gly
        275                 280                 285

Asp Thr Ile Ser Ser Cys Pro Ser Ala Ser Ala Tyr Gly Gly Leu Ala
290                 295                 300

Thr Met Gly Lys Ala Leu Ser Asp Gly Met Val Leu Ile Phe Ser Ile
305                 310                 315                 320

Trp Asn Asp Asn Ser Gln Tyr Met Asn Trp Leu Asp Ser Gly Glu Ala
                325                 330                 335

Gly Pro Cys Ser Ser Thr Glu Gly Asn Pro Ser Asn Ile Leu Ala Asn
            340                 345                 350

Asn Pro Gly Thr His Val Val Tyr Ser Asn Ile Arg Trp Gly Asp Ile
        355                 360                 365

Gly Ser Thr Thr Asn Ser Thr Gly Gly Asn Pro Pro Pro Pro Pro Ala
370                 375                 380

Ser Ser Thr Thr Phe Ser Thr Thr Arg Arg Ser Ser Thr Thr Ser Ser
385                 390                 395                 400

Ser Pro Ser Cys Thr Gln Thr His Trp Gly Gln Cys Gly Gly Ile Gly
```

```
                405                 410                 415

Tyr Thr Gly Cys Lys Thr Cys Thr Ser Gly Thr Thr Cys Gln Tyr Gly
            420                 425                 430

Asn Asp Tyr Tyr Ser Gln Cys Leu
            435                 440

<210> SEQ ID NO 12
<211> LENGTH: 440
<212> TYPE: PRT
<213> ORGANISM: artificial
<220> FEATURE:
<223> OTHER INFORMATION: artificial construct

<400> SEQUENCE: 12

Ser Gln Gln Pro Gly Thr Ser Thr Pro Glu Val His Pro Lys Leu Thr
1               5                   10                  15

Thr Tyr Lys Cys Thr Thr Ser Gly Gly Cys Val Ala Gln Asn Thr Ser
            20                  25                  30

Val Val Leu Asp Trp Asn Tyr Arg Trp Met His Asp Ala Asn Tyr Asn
        35                  40                  45

Ser Cys Thr Val Asn Gly Gly Val Asn Thr Thr Leu Cys Pro Asp Glu
    50                  55                  60

Ala Thr Cys Gly Lys Asn Cys Phe Ile Glu Gly Val Asp Tyr Ala Ala
65                  70                  75                  80

Ser Gly Val Thr Ala Ser Gly Ser Thr Leu Thr Leu Asn Gln Tyr Met
                85                  90                  95

Pro Ser Ser Ser Gly Gly Tyr Ser Val Ser Pro Arg Leu Tyr Leu Leu
            100                 105                 110

Leu Gly Pro Asp Gly Lys Tyr Val Met Leu Lys Leu Asn Gly Gln Glu
        115                 120                 125

Leu Ser Phe Asp Val Asp Leu Ser Ala Leu Pro Cys Gly Glu Asn Ala
130                 135                 140

Ser Leu Tyr Leu Ser Gln Met Asp Glu Asn Gly Gly Ala Asn Gln Tyr
145                 150                 155                 160

Asn Thr Ala Gly Ala Asn Tyr Gly Ser Gly Tyr Cys Asp Ala Gln Cys
                165                 170                 175

Pro Val Gln Thr Trp Arg Asn Gly Thr Leu Asn Thr Ser Gly Gln Gly
            180                 185                 190

Phe Cys Cys Asn Glu Met Asp Ile Leu Glu Gly Asn Ser Arg Ala Asn
        195                 200                 205

Ala Leu Thr Pro His Ser Cys Asn Ala Thr Ala Cys Asp Ser Ala Gly
    210                 215                 220

Cys Gly Phe Asn Pro Tyr Lys Ser Gly Tyr Pro Asn Tyr Phe Gly Pro
225                 230                 235                 240

Gly Gly Thr Val Asp Thr Ser Lys Pro Phe Thr Ile Ile Thr Gln Phe
                245                 250                 255

Asn Thr Asp Asn Gly Ser Pro Ser Gly Asn Leu Val Ser Ile Thr Arg
            260                 265                 270

Lys Tyr Arg Gln Asn Gly Val Asp Ile Pro Ser Ala Lys Pro Gly Gly
        275                 280                 285

Asp Thr Ile Ser Ser Cys Pro Ser Ala Ser Ala Tyr Gly Gly Leu Ala
    290                 295                 300

Thr Met Gly Lys Ala Leu Ser Asp Gly Met Val Leu Ile Phe Ser Ile
305                 310                 315                 320

Trp Asn Asp Asn Ser Gln Tyr Met Asn Trp Leu Asp Ser Gly Ser Ala
```

```
                    325                 330                 335
Gly Pro Cys Ser Ser Thr Glu Gly Asn Pro Ser Asn Ile Leu Ala Asn
                340                 345                 350

Asn Pro Gly Thr His Val Val Tyr Ser Asn Ile Arg Trp Gly Asp Ile
            355                 360                 365

Gly Ser Thr Thr Asn Ser Thr Gly Gly Asn Pro Pro Pro Pro Pro Ala
        370                 375                 380

Ser Ser Thr Thr Phe Ser Thr Thr Arg Arg Ser Ser Thr Thr Ser Ser
385                 390                 395                 400

Ser Pro Ser Cys Thr Gln Thr His Trp Gly Gln Cys Gly Gly Ile Gly
                405                 410                 415

Tyr Thr Gly Cys Lys Thr Cys Thr Ser Gly Thr Thr Cys Gln Tyr Gly
            420                 425                 430

Asn Asp Tyr Tyr Ser Gln Cys Leu
        435                 440

<210> SEQ ID NO 13
<211> LENGTH: 440
<212> TYPE: PRT
<213> ORGANISM: artificial
<220> FEATURE:
<223> OTHER INFORMATION: artificial construct

<400> SEQUENCE: 13

Ser Gln Gln Pro Gly Thr Ser Thr Pro Glu Val His Pro Lys Leu Thr
1               5                   10                  15

Thr Tyr Lys Cys Thr Thr Ser Gly Gly Cys Val Ala Gln Asp Thr Ser
            20                  25                  30

Val Val Leu Asp Trp Asn Tyr Arg Trp Ile His Asp Ala Asn Tyr Asn
        35                  40                  45

Ser Cys Thr Val Asn Gly Gly Val Asn Thr Thr Leu Cys Pro Asp Glu
    50                  55                  60

Ala Thr Cys Ser Lys Asn Cys Phe Ile Glu Gly Val Asp Tyr Ala Ala
65                  70                  75                  80

Ser Gly Val Thr Ala Asn Gly Ser Thr Leu Thr Leu Asn Gln Tyr Met
                85                  90                  95

Pro Ser Ser Ser Gly Gly Tyr Ser Ser Val Ser Pro Arg Leu Tyr Leu
            100                 105                 110

Leu Gly Pro Asp Gly Glu Tyr Val Met Leu Lys Leu Asn Gly Gln Glu
        115                 120                 125

Leu Ser Phe Asp Val Asp Leu Ser Ala Leu Pro Cys Gly Glu Asn Gly
    130                 135                 140

Ser Leu Tyr Leu Ser Gln Met Asp Glu Asn Gly Gly Ala Asn Gln Tyr
145                 150                 155                 160

Asn Thr Ala Gly Ala Asn Tyr Gly Ser Gly Tyr Cys Asp Ala Gln Cys
                165                 170                 175

Pro Val Gln Thr Trp Arg Asn Gly Thr Leu Asn Thr Ser Gly Gln Gly
            180                 185                 190

Phe Cys Cys Asn Glu Met Asp Ile Leu Glu Gly Asn Ser Arg Ala Asn
        195                 200                 205

Ala Leu Thr Pro His Ser Cys Thr Ala Thr Ala Cys Asp Ser Ala Gly
    210                 215                 220

Cys Gly Phe Asn Pro Tyr Gly Ser Gly Tyr Pro Asn Tyr Phe Gly Pro
225                 230                 235                 240

Gly Asp Thr Val Asp Thr Ser Lys Pro Phe Thr Ile Ile Thr Gln Phe
```

```
                    245                 250                 255
Asn Thr Asp Asn Gly Ser Pro Ser Gly Asn Leu Val Ser Ile Thr Arg
            260                 265                 270

Lys Tyr Arg Gln Asn Gly Val Asp Ile Pro Ser Ala Lys Pro Gly Gly
        275                 280                 285

Asp Thr Ile Ser Ser Cys Pro Ser Ala Ser Ala Tyr Gly Gly Leu Ala
        290                 295                 300

Thr Met Gly Lys Ala Leu Ser Ser Gly Met Val Leu Ile Phe Ser Ile
305                 310                 315                 320

Trp Asn Asp Asn Ser Gln Tyr Met Asn Trp Leu Asp Ser Gly Ser Ala
                325                 330                 335

Gly Pro Cys Ser Ser Thr Glu Gly Asn Pro Ser Asn Ile Leu Ala Asn
            340                 345                 350

Asn Pro Gly Thr His Val Val Tyr Ser Asn Ile Arg Trp Gly Asp Ile
                355                 360                 365

Gly Ser Thr Thr Asn Ser Thr Gly Gly Asn Pro Pro Pro Pro Pro Ala
        370                 375                 380

Ser Ser Thr Thr Phe Ser Thr Thr Arg Arg Ser Ser Thr Thr Ser Ser
385                 390                 395                 400

Ser Pro Ser Cys Thr Gln Thr His Trp Gly Gln Cys Gly Gly Ile Gly
                405                 410                 415

Tyr Thr Gly Cys Lys Thr Cys Thr Ser Gly Thr Thr Cys Gln Tyr Gly
            420                 425                 430

Asn Asp Tyr Tyr Ser Gln Cys Leu
        435                 440

<210> SEQ ID NO 14
<211> LENGTH: 440
<212> TYPE: PRT
<213> ORGANISM: artificial
<220> FEATURE:
<223> OTHER INFORMATION: artificial construct

<400> SEQUENCE: 14

Ser Gln Gln Pro Gly Thr Ser Thr Pro Glu Val His Pro Lys Leu Thr
1               5                  10                  15

Thr Tyr Lys Cys Thr Thr Ser Gly Gly Cys Val Ala Gln Asp Thr Ser
            20                  25                  30

Val Val Leu Asp Trp Asn Tyr Arg Trp Ile His Asp Ala Asn Tyr Asn
        35                  40                  45

Ser Cys Thr Val Asn Gly Gly Val Asn Thr Thr Leu Cys Pro Asp Glu
    50                  55                  60

Ala Thr Cys Gly Lys Asn Cys Phe Ile Glu Gly Val Asp Tyr Ala Ala
65                  70                  75                  80

Ser Gly Val Thr Ala Asn Gly Ser Thr Leu Thr Leu Asn Gln Tyr Met
                85                  90                  95

Pro Ser Ser Ser Gly Gly Tyr Ser Val Ser Pro Arg Leu Tyr Leu
            100                 105                 110

Leu Gly Pro Asp Gly Glu Tyr Val Met Leu Lys Leu Asn Gly Gln Glu
        115                 120                 125

Leu Ser Phe Asp Val Asp Leu Ser Ala Leu Pro Cys Gly Glu Asn Gly
    130                 135                 140

Ser Leu Tyr Leu Ser Gln Met Asp Glu Asn Gly Gly Ala Asn Gln Tyr
145                 150                 155                 160

Asn Thr Ala Gly Ala Asn Tyr Gly Ser Gly Tyr Cys Asp Ala Gln Cys
```

```
                165                 170                 175
Pro Val Gln Thr Trp Arg Asn Gly Thr Leu Asn Thr Ser Gly Gln Gly
            180                 185                 190

Phe Cys Cys Asn Glu Met Asp Ile Leu Glu Gly Asn Ser Arg Ala Asn
        195                 200                 205

Ala Leu Thr Pro His Ser Cys Thr Ala Thr Ala Cys Asp Ser Ala Gly
    210                 215                 220

Cys Gly Phe Asn Pro Tyr Gly Ser Gly Tyr Pro Asn Tyr Phe Gly Pro
225                 230                 235                 240

Gly Asp Thr Val Asp Thr Ser Lys Pro Phe Thr Ile Thr Gln Phe
                245                 250                 255

Asn Thr Asp Asn Gly Ser Pro Ser Gly Asn Leu Val Ser Ile Thr Arg
            260                 265                 270

Lys Tyr Arg Gln Asn Gly Val Asp Ile Pro Ser Ala Lys Pro Gly Gly
        275                 280                 285

Asp Thr Ile Ser Ser Cys Pro Ser Ala Ser Ala Tyr Gly Gly Leu Ala
    290                 295                 300

Thr Met Gly Lys Ala Leu Ser Ser Gly Met Val Leu Ile Phe Ser Ile
305                 310                 315                 320

Trp Asn Asp Asn Ser Gln Tyr Met Asn Trp Leu Asp Ser Gly Ser Ala
                325                 330                 335

Gly Pro Cys Ser Ser Thr Glu Gly Asn Pro Ser Asn Ile Leu Ala Asn
            340                 345                 350

Asn Pro Gly Thr His Val Val Tyr Ser Asn Ile Arg Trp Gly Asp Ile
        355                 360                 365

Gly Ser Thr Thr Asn Ser Thr Gly Gly Asn Pro Pro Pro Pro Ala
    370                 375                 380

Ser Ser Thr Thr Phe Ser Thr Thr Arg Arg Ser Ser Thr Thr Ser Ser
385                 390                 395                 400

Ser Pro Ser Cys Thr Gln Thr His Trp Gly Gln Cys Gly Gly Ile Gly
                405                 410                 415

Tyr Thr Gly Cys Lys Thr Cys Thr Ser Gly Thr Thr Cys Gln Tyr Gly
            420                 425                 430

Asn Asp Tyr Tyr Ser Gln Cys Leu
        435                 440

<210> SEQ ID NO 15
<211> LENGTH: 1620
<212> TYPE: DNA
<213> ORGANISM: artificial
<220> FEATURE:
<223> OTHER INFORMATION: artificial construct

<400> SEQUENCE: 15
atgagatttc cttcaatttt tactgcagtt ttattcgcag catcctccgc attagctgct    60
ccagtcaaca ctacaacaga agatgaaacg gcacaaattc cggctgaagc tgtcatcggt   120
tacttagatt tagaagggga tttcgatgtt gctgttttgc cattttccaa cagcacaaat   180
aacgggttat tgtttataaa tactactatt gccagcattg ctgctaaaga agaagggta   240 tctttggata acgtgaggc ggaagcatgc caccaccacc accaccactc ctccggctct   300
ctgcagccag gaacttctac tccagaggtg cacccaaagc tgaccaccta caagtgtacc   360
acctctggtg gttgtgttgc tcagaacacc tatgttgttc tggactggaa ctacagatgg   420
atccacgacg ccaactacaa ctcttgtacc gtgaacggtg tgtcaacac tactctgtgt   480
```

```
ccagacgagg ctactggtag caagaactgc ttcatcgagg gtgttgacta cgctgcttct      540
ggtgttactg ccaatggttc taccttgacc ctgaaccagt acatgccatc ttcctctggc      600
ggttacactt ctgtgtcgcc aagactgtac ttgttgggtc cagacggtaa gtacgttatg      660
ctgaagctga acggacagga gctgtctttt gacgttgacc tgtctgcttt gccatgtgga      720
gagaacgctt ctctgtacct gtctcagatg gacgagaacg gtggagctaa ccagtacaac      780
accgccggtg ctaactacgg ttctggttac tgtgacgccc agtgtccagt tcagacttgg      840
agaaacggaa ccctgaacac ttctggccag ggattctgct gtaacgagat ggacatcttg      900
gagggaaact ctagagctaa cgctctgacc ccacactctt gtaatgctac cgcttgtgac      960
tctgctggtt gcggttttaa cccataccgc tcgggttacc caaactactt tggcccaggt     1020
ggcactgttg acacctcgaa gccattcacc atcatcaccc agttcaacac cgacaacggt     1080
tctccatctg gtaacctggt gtcgatcacc agaaagtaca gacagaacgg cgttgacatc     1140
ccatctgcta aaccaggtgg cgacaccatt tcgtcttgtc catctgcctc tacttacggt     1200
ggattggcta ccatgggaaa ggctctgtcc gagggaatgg tgctgatctt ctcgatctgg     1260
aacgacaact cgcagtacat gaactggctg gactctggtg atgctggtcc atgttcttct     1320
accgagggca acccatctaa catcctggct aacaaccctg gtactcacgt ggtgtactcg     1380
aacattagat ggggcgacat tggttctacc accaactcta ccggtggtaa cccaccacca     1440
ccacctgcat cttctaccac cttctcgacc gccagaagat cgtctacctc ctcttcttct     1500
ccatcttgta tccagactca ctggggtcag tgtggtggta ttggctacac cggctgtaag     1560
acctgtacct ctggaaccac ttgccagtac agcaacgact actactctca gtgcctgtga     1620
```

<210> SEQ ID NO 16
<211> LENGTH: 1368
<212> TYPE: DNA
<213> ORGANISM: artificial
<220> FEATURE:
<223> OTHER INFORMATION: artificial construct

<400> SEQUENCE: 16

```
atgtatcgga agttggccgt catctcggcc ttcttggcca cagcacgggc ttctctgcaa       60
ccgggtacca gcaccccga ggtccatccc aagttgacaa cctacaagtg tacaacctcc      120 gggggtgcg tggcccagaa cacctatgtg gtccttgact ggaactaccg ctggatccac      180 gacgcaaaact acaactcgtg caccgtcaac ggcggcgtca acaccacgct ctgccctgac      240
gaggcgaccg gtagcaagaa ctgcttcatc gagggcgtcg actacgccgc tcgggcgtc       300 acggccaatg gcagcaccct caccctgaac cagtacatgc ccagcagctc tggcggctac      360
actagcgtct ctcctcggct gtatctcctg ggtccagacg gtaagtacgt gatgctgaag      420
ctcaacggcc aggagctgag cttcgacgtc gacctctctg ctctgccgtg tggagagaac      480
gcctcgctct acctgtctca gatggacgag aacggggggcg ccaaccagta taacacggcc      540
ggtgccaact acgggagcgg ctactgcgat gctcagtgcc ccgtccagac atggaggaac      600 ggcacccctca acactagcgg ccagggcttc tgctgcaacg agatggatat cctggagggc      660
aactcgaggg cgaatgcctt gaccccctcac tcttgcaatg ccacgccctg cgactctgcc      720
ggttgcggct tcaaccccta tcgcagcggc tacccaaact acttcggccc cggaggcacc      780
gttgacacct ccaagccatt caccatcatc acccagttca acacggacaa cggctcgccc      840
tcgggcaacc ttgtgagcat caccccgcaag tacagacaaa acggcgtcga catccccagc      900
gccaaacccg gcggcgacac catctcgtcc tgcccgtccg cctcaactta cggcggcctc      960
```

-continued

```
gccaccatgg gcaaggccct gagcgagggc atggtgctca tcttcagcat ttggaacgac      1020
aacagccagt acatgaactg gctcgacagc ggcgatgccg gcccctgcag cagcaccgag      1080
ggcaacccat ccaacatcct ggccaacaac cccggtacgc acgtcgtcta ctccaacatc      1140
cgctggggag acattgggtc tactacgaac tcgactggtg gtccgccccc gcctgcgtcc      1200
agcacgacgt tttcgactgc ccggaggagc tcgacgtcct cgagcagccc gagctgcatc      1260
cagactcact gggggcagtg cggtggcatt gggtacaccg ggtgcaagac gtgcacgtcg      1320
ggcactacgt gccagtatag caacgactac tactcgcaat gcctttaa               1368
```

ENDOGLUCANASES WITH IMPROVED PROPERTIES

CROSS REFERENCE TO RELATED APPLICATIONS

This application claims the priority of PCT/EP2013/058985, filed on 30 Apr. 2013, which claims priority to EP 12166458.5 filed on 2 May 2012, the entire contents of each of which are hereby incorporated in total by reference.

SEQUENCE LISTING

This application incorporates by reference the Sequence Listing contained in an ASCII text file named "366746-00004SequenceListing" submitted via EFS-Web. The text file was created on Oct. 28, 2014, and is 53.0 kb in size.

FIELD OF THE INVENTION AND BACKGROUND ART

Cellulose is a major component of plant material. It is the basis for the structural integrity of plants and is often found in a lignocellulose matrix composed of cellulose, hemicelluloses, and lignin. Applications employing cellulose take advantage of either its structural properties (fibers, textiles, paper, etc.) or of its carbohydrate nature, producing D-glucose, cellobiose and/or cellulose oligomers.

Lignocelluloses are readily available from agriculture and forestry including byproduct streams from cereals, corn, sugar cane, sugar beet, timber, etc. Plants that are optimized for their lignocellulose content and yield ("energy crops") will likely contribute as an important resource in the near future.

Cellulases comprise a structurally and functionally diverse class of glycohydrolases acting on cellulose. Cellulases are found in bacteria, archea, fungi and plants. Having in common the hydrolytic cleavage activity of glycosidic bonds present in cellulose polymers or oligomers, they differ in substrate specificity, mode of action, and enzyme parameters, including processivity, pH and temperature optima. Most cellulases act on β-1,4-linkages between two glucose moieties. However other linkages found in lignocelluloses may also be hydrolysed. Cellulases can be subdivided by their mode of action into endo- and exo-enzymes. Endoglucanases introduce random cleavages into the cellulose polymer, thereby reducing the degree of polymerization. Exo-enzymes, like cellobiohydrolases, work in a successive mode of action, releasing cellobiose (D-glucose-β-1,4-D-glucopyranoside) from the reducing or non-reducing end of the polymer.

The CAZY Database [Cantarel B L, Coutinho P M, Rancurel C, Bernard T, Lombard V, Henrissat B (2009) The Carbohydrate-Active EnZymes database (CAZy): an expert resource for Glycogenomics. Nucleic Acids Res 37:D233-238 PMID: 18838391] holds, amongst others, a collection of known glucohydrolases including cellulose degrading enzymes (i.e. cellulases). In this database enzymes are classified to different GH-classes according to structural elements. Several GH classes include endoglucanases, in particular the classes GH5, GH7, GH9, GH12, GH16, GH45, GH48, GH61 and GH74. Despite the high diversity within some of the GH classes, members of one GH class often have similar physical and enzymatic parameters. This allows general statements to be made like substrate specificity, pH range, stability, or catalytic efficiency for members of a certain GH class.

Cellulose-degrading microorganisms often produce and secrete a complex mixture of cellulases. For instance, in the secretome of *Trichoderma reesei* 7 endoglucanases have been identified belonging to 6 different GH classes (Cel5A, Cel7B, Cel12A, Cel45A, Cel61A, Cel61B, Cel74A). The different endoglucanases show a spectrum of properties (Karlsson J, Siika-aho M, Tenkanen M, Tjerneld F. Enzymatic properties of the low molecular mass endoglucanases Cel12A (EG III) and Cel45A (EG V) of *Trichoderma reesei*. J Biotechnol. 2002 Oct. 9; 99(1):63-78. PubMed PMID: 12; Karlsson J, Momcilovic D, Wittgren B, Schülein M, Tjerneld F, Brinkmalm G. Enzymatic degradation of carboxymethyl cellulose hydrolyzed by the endoglucanases Cel5A, Cel7B, and Cel45A from *Humicola insolens* and Cel7B, Cel12A and Cel45Acore from *Trichoderma reesei*. Biopolymers. 2002 January; 63(1):32-40. PubMed PMID: 11754346.). The two predominant endoglucanases, EGI (Cel7B, GH7) and EGII (Cel5A), are considered to be the most active enzymes thereof.

The synergistic activity of cellulolytic enzymes allows the efficient breakdown of complex substrates (B. Henrissat, H. Driguez, C. Viet & M. Schülein: Synergism of Cellulases from *Trichoderma reesei* in the Degradation of Cellulose; Nature Biotechnology 3, 722-726 (1985) doi:10.1038/nbt0885-722) and precludes the replacement of a component of one structural class by an enzyme from a second fold, when at the same time the hydrolytic efficiency needs to be kept at maximum level (Non-equivalency of different EGs). A simple replacement by another GH class enzyme is not always possible. Generally speaking, members of endoglucanases from the GH5 family (including EGs from thermophilic bacteria) show higher thermostability compared to endoglucanases of the GH7 family; nevertheless, the application of a thermostable GH7 family protein is often advantageous for high hydrolysis rates.

Many applications of endoglucanases were reported, as part of complex enzyme mixtures as single enzyme activities. Cellulases are important for making cellulose-derived biofuels. After cutting and, optionally, chemical and/or physical pretreatment, lignocelluloses are incubated with cellulases to release sugar monomers that are further processed. Process conditions need to be adapted to optimize hydrolysis rates, yields and/or stability. Higher temperatures are often preferred in these processes but require more thermostable enzymes. Simultaneous saccharification and hydrolysis (SSF) processes require cellulolytic enzymes that are active under fermentative conditions. Consolidated bioprocessing (CBP) further requires the combination of enzyme properties, in order to have enzyme production, saccharification and fermentation done in a single step.

Other applications of endoglucanases aim only on a partial hydrolysis or modification of cellulose fibers (fiber modification, biopolishing, biostoning, etc.). Endoglucanases used therefore need to work and/or be stable at elevated temperatures, extreme (e.g. alkaline, acid) pH, and chemical conditions (e.g. laundry, detergents, proteases, solvents, etc.). Fiber damage must be minimized for such applications. Endoglucanases can also assist in the separation of non-cellulosic fractions from the fiber material in pulping processes (pulp & paper production) or improve rheological properties of process streams. Detergent stability and protease resistance can be seen as a product of increased stability of the enzyme structure, a property that is also connected to increased thermal stability. Endoglucanases also find applications in food and feed processing (breweries, wine production, oil recovery from press cake, baking, dough preparation. Often sterilization or pasteurization requires higher temperatures. For shortening of processing times the operational stability of the endoglucanase can be advantageous.

Endoglucanase I proteins (Cel7B) derived from fungi of the genus *Trichoderma* (anamorph *Hypocrea*) show high degrees of identity and are considered mesophilic. The most stable members of endoglucanases from the GH family 7 reported are native enzymes from *Humicola insulens* (Cel7B) and *Fusarium oxysporum* (eg1) (U.S. Pat. No. 5,912,157). According to said report, EGI does not exhibit activity above 60° C. There is thus a need in the field for the provision of more thermostable endoglucanases from the GH family 7.

It was reported that some endoglucanases can be thermally inactivated at higher temperatures (Dominguez J M, Acebal C, Jimenez J, de la Mata I, Macarron R, Castillon M P. Mechanisms of thermoinactivation of endoglucanase I from *Trichoderma reesei* QM 9414. Biochem J. 1992 Oct. 15; 287 (Pt 2):583-8.). The authors of said study also attempted re-activation of thermoinactivated endoglucanase, but this required harsh conditions involving 8 M urea and further agents. Effects described as productive refolding were shown on other proteins than endoglucanases [Zhang N, Suen W C, Windsor W, Xiao L, Madison V, Zaks A. Improving tolerance of *Candida antarctica* lipase B towards irreversible thermal inactivation through directed evolution. Protein Eng. 2003 August; 16(8):599-605.], but to the knowledge of the inventors not for endoglucanases, in particular endoglucanases of GH7. It is believed in the art that thermoinactivated endoglucanases are of little use in industrial breakdown of cellulose. On the other hand, elevated thermostability is often desired for endoglucanases, in particular for enzymes of fungal origin. So far, only some improvements for endoglucanases of GH12 and GH45 were reported. Thermostable endoglucanases have been reported from the structural folds of GH5 and GH48. Said endoglucanases substantially differ with respect to their kinetic properties and substrate preference from the endoglucanases of the GH7 class.

In summary, there is a need for processive endoglucanases, particularly of the GH7 family, with superior temperature profiles. It would furthermore be desirable to achieve good productivity from their expression host. The need is further supported by the fact that many processes of industrial relevance run under harsh conditions and at elevated temperatures. A problem to be solved by the present invention is the provision of improved endoglucanases, particularly of endoglucanases with improved thermal properties. Further problems addressed and solved by this invention will become apparent from the sections below.

SUMMARY OF THE INVENTION

The invention relates to thermostable endoglucanase proteins (polypeptides). The solutions provided are:
1. A protein having endoglucanase activity which belongs to the GH7 class and which shows active thermostabilization.
2. A protein having endoglucanase activity which comprises an amino acid sequence having at least 96%, preferably at least 97%, more preferably at least 98%, even more preferably at least 99%, such as at least 99.5% identity to SEQ. ID NO.: 2.

Preferably, the endoglucanase proteins of the invention show more than 95% residual activity at 60° C.

A further aspect of the invention are nucleic acids encoding said polypeptides and expression constructs comprising these polynucleotides in a vector backbone contained in an organism. Another aspect of the invention is the application of the proteins of the invention for the processing of lignocellulose and cellulose materials. In particular, saccharification of lignocellulose feedstock in consolidated, partially consolidated or non-consolidated processes, or in the processing of food, feed, cellulose fiber, or cleaning applications.

The invention also relates to production/expression organisms for the production of the proteins of the invention and to processes for the cultivation of such organisms for the purpose of protein production. The organisms are selected from organisms including microorganisms (fungal, bacterial, or archea) or plants.

DEFINITIONS

Figure 1:
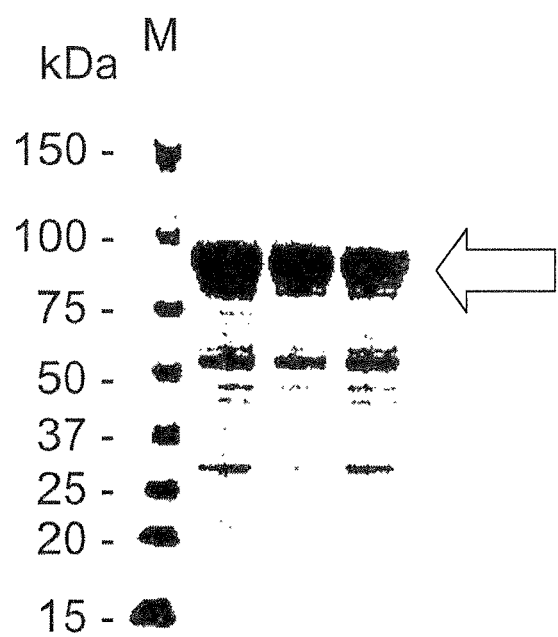
FIG. 1: The SDS-gel shows the expression of a Seq. ID NO 8—a Seq. ID NO 2 variant—protein secreted into the supernatant. The band of the expressed protein is visible between 75 and 100 kDa.

"Thermostability" is a term used to describe an intrinsic property of a particular protein with endoglucanase activity according to the present invention.

"Active thermostabilization" is a term used to describe an intrinsic property of a particular protein with endoglucanase activity according to the present invention.

Determination of thermostability and/or active thermostabilization: Thermostability and active thermostabilization are determined as follows.

1.) The enzyme is expressed in *Pichia pastoris* as described in Example 2. The enzyme is optionally purified.

2.) Adjustment of the enzyme concentration

An enzyme solution of an appropriate concentration is made by dilution of purified enzyme or *Pichia pastoris* culture supernatant in sodium acetate buffer (50 mM, pH 5) to an applicable working concentration. For determination of the applicable working concentration, a serial dilution of the enzyme obtained in step 1) above is prepared in the sodium acetate buffer and 10 μl aliquots are tested in the temperature gradient as described in Example 4. An applicable working concentration is defined as a concentration which results in a fluorescence signal between 5,000 and 15,000 in a Tecan Infinite M200 plate-reader at gain 50, or an equivalent concentration of 5.4 µM to 19 µM 4-Methylumbelliferon after incubation as described in o Example 4.

3.) Determination of the substrate conversion capacity as described in Example 4, with the exception that the 10 µl aliquot of the culture supernatant is replaced by the 10 µl aliquot of the enzyme solution in applicable working concentration as defined in step 2).

4.) Normalization of the measurement by division of all relative fluorescence unit (rfu) reads by the maximum rfu read within the temperature gradient to obtain a relative substrate conversion for each protein tested at each temperature tested.

5.) Plotting of the relative substrate conversion vs. the tested reaction temperatures.

6.) Determination of the temperature stability as described in (a) or determination of active thermostabilization as described in (b) as follows.

a. Determination of temperature stability: a protein is characterized temperature stable if the relative substrate conversion at 60° C. is 0.5 or more, preferably 0.7 or more and more preferably 0.9 or more, such as 0.95 or more.

Determination of active thermostabilization: Analysis of the plot obtained in step 5) for the presence of a plateau at a relative substrate conversion which is lower than the maximum level (which is 1), but which is at least as high as 0.15.

A plateau is defined as a level of the relative substrate conversion which is essentially unchanged within a temperature range of at least 5° C., preferably from 70 to 75° C. (i.e. within +/−0.1 around the average value within said temperature range).

b. Variants showing no active thermostabilization have a relative substrate conversion between 0 and lower than 0.15, usually around 0.1. Without wishing to be bound to any particular theory, it is believed that the measured relative substrate conversion of usually around 0.1 (rather than 0.0, as expected for an inactive enzyme at a given temperature) is due to finite temperature ramps in the thermocycler and/or during handling of the sample mixtures.

Thermal properties is a term generally used to refer to the properties of an enzyme at higher temperatures (e.g. 60° C. or more). The term can include one or both of "temperature stability" as defined above and "active thermostabilization" as described above.

Endoglucanase activity in the context of this invention is defined as the catalytic acceleration of the breakage of β-1,4-glucosidic bonds via nucleophilic attack by a polar molecule as water or organic molecules with their hydroxyl- or mercapto- or amino-functions, by a protein. The definition also includes the cleavage of synthetic molecules having a non-carbohydrate molecule linked to glucose, cellobiose or lactose, via β-1,4-glycosidic linkage. Example reactions catalyzed by endoglucanases are listed by the Brenda Database (http://www.brenda-enzymes.info (Release 2012.1 (January 2012)); Enzyme data and metabolic information: BRENDA, a resource for research in biology, biochemistry, and medicine Schomburg, I., Hofmann, O., Baensch, C., Chang, A., Schomburg, D. *Gene Funct*. *Dis*. 3-4, 109-18 (2000))

Residual activity is defined as the enzymatic activity that is recovered after incubation of the enzyme for a defined time at a defined (elevated) temperature in comparison to the activity without the incubation step. A protocol for the determination of the residual activity is given in Example 4.

Sequence Alignment with SEQ ID NO: 2: Pairwise alignment of any second GH7 endoglucanase sequence with the parental sequence (SEQ ID NO 2) is done using the ClustalW Algorithm (Larkin M. A., Blackshields G., Brown N. P., Chenna R., McGettigan P. A., McWilliam H., Valentin F., Wallace I. M., Wilm A., Lopez R., Thompson J. D., Gibson T. J. and Higgins D. G. (2007) ClustalW and ClustalX version 2. Bioinformatics 2007 23(21): 2947-2948). The pairwise alignment will show position numbers for SEQ ID NO: 2. Said numbers can be used for reference, for example when saying that, e.g. the residue corresponding to position no. 2 of SEQ ID NO: 2 is mutated in the second GH7 endoglucanase. As convention for numbering of amino acids and designation of protein variants for the description of protein variants the amino acid within the parental protein sequence SEQ ID NO: 2 is referred to as position number 1 or S1 or serine 1. The numbering of all amino acids will be according to their position in the parental sequence given in SEQ ID NO: 2 relative to this position number 1.

Sequence identity: For determination of Sequence Identity the software AlignX from the VectorNTI Package sold by Life Technology Corporation is used, using the standard settings (Gap opening penalty 10, Gap extension penalty 0.1).

Protein variants are polypeptides whose amino acid sequence differs in one or more positions from this parental protein, whereby differences might be replacements of one amino acid residue(s) by another, deletions of single or several amino acid residue(s), or insertion of additional amino acid residue(s) or stretches of amino acid residue(s) into the parental sequence. Proteins can be modified at defined positions by introduction of point mutations into the encoding nucleic acids. The term modified protein sequence herein always refers to proteins resulting from transcription and translation as well as optional post-translational modification and translocation processes from correspondingly modified nucleic acids, either in vitro or by a suitable expression host. Methods for the generation of such protein variants are well known in the art and thus not limited, examples include random or site directed mutagenesis, site-saturation mutagenesis, PCR-based fragment assembly, DNA shuffling, homologous recombination in vitro or in vivo, and methods of gene-synthesis based on chemical DNA synthesis.

The nomenclature of amino acids, peptides, nucleotides and nucleic acids is done according to IUPAC. Generally amino acids are named within this document according to the one letter code.

Exchanges of single amino acids are described by naming the single letter code of the original amino acid followed by its position number and the single letter code of the replacing amino acid, i.e. the change of glutamine at position one to a leucine at this position is described as "Q1L". For deletions of single positions from the sequence the symbol of the replacing amino acid is substituted by the three letter abbreviation "del" thus the deletion of alanine at position 3 would be referred to as "A3del". Inserted additional amino acids receive the number of the preceding position extended by a small letter in alphabetical order relative to their distance to their point of insertion. Thus, the insertion of two tryptophanes after position 3 is referred to as "3aW, 3bW". Introduction of untranslated codons TAA, TGA and TAG into the nucleic acid sequence is indicated as "*" in the amino acid sequence, thus the introduction of a terminating codon at position 4 of the amino acid sequence is referred to as "G4*". Multiple mutations are separated by a plus sign or a slash or a comma. For example, two mutations in positions 20 and 21 substituting alanine and glutamic acid for glycine and serine, respectively, are indicated as "A20G+E21S" or "A20G/E21S" "A20G,E21S". When an amino acid residue at a given position is substituted with two or more alternative amino acid residues these residues are separated by a comma or a slash. For example, substitution of alanine at position 30 with either glycine or glutamic acid is indicated as "A20G, E" or "A20G/E", or "A20G, A20E". When a position suitable for modification is identified herein without any specific modification being suggested, it is to be understood that any amino acid residue may be substituted for the amino acid residue present in the position. Thus, for instance, when a modification of an alanine in position 20 is mentioned but not specified, it is to be understood that the alanine may be deleted or substituted for any other amino acid residue (i.e. any one of R, N, D, C, Q, E, G, H, I, L, K, M, F, P, S, T, W, Y and V).

The terms "similar mutation" or "similar substitution" refer to an amino acid mutation wherein an amino acid residue in a first mutation (with respect to the parental sequence, such as e.g. SEQ ID NO: 2) is replaced again by a second mutation, and whereby the amino acid residue brought in by the second mutation has similar properties to the amino acid residue that had been brought in by the first mutation. Similar in this context means an amino acid that has similar chemical properties. If, for example, a first mutation at a specific position leads to a substitution of a non-aliphatic amino acid residue (e.g. Ser) with an aliphatic amino acid residue (e.g. Leu), then a substitution at the same position with a different aliphatic amino acid by means of a second mutation (e.g. Ile or Val) is referred to as a similar mutation. Further chemical properties include size of the residue, hydrophobicity, polarity, charge, pK-value, and the like. Thus, a similar mutation may include substitution such as basic for basic, acidic for acidic, polar for polar etc. The sets of amino acids thus derived are likely to be conserved for structural reasons. These sets can be described in the form of a Venn diagram (Livingstone C D. and Barton G J. (1993) "Protein sequence alignments: a strategy for the hierarchical analysis of residue conservation" Comput. Appl Biosci. 9: 745-756; Taylor W. R. (1986) "The classification of amino acid conservation" J. Theor. Biol. 119; 205-218). Similar substitutions may be made, for example, according to the following grouping of amino acids: Hydrophobic: F W Y H K M I L V A G; Aromatic: F W Y H; Aliphatic: I L V; Polar: W Y H K R E D C S T N; Charged H K R E D; Positively charged: H K R; Negatively charged: E D.

An expression construct herein is defined as a DNA sequence comprising all required sequence elements for establishing expression of an comprised open reading frame (ORF) in the host cell including sequences for transcription initiation (promoters), termination and regulation, sites for translation initiation, regions for stable replication or integration into the host genome and a selectable genetic marker. The open reading frame optionally consists of a fusion of a nucleic acid coding for the target protein with further elements, especially secretion signals, a cellulose binding domain, TAGs for enhancement of the expression level or facilitation of purification or isolation from the fermentation broth. The functional setup thereby can be already established or reached by arranging (integration etc.) event in the host cell. In a preferred embodiment the expression construct contains a promoter functionally linked to the open reading frame followed by an optional termination sequence. Preferred promoters are medium to high strength promoters, functional in the selected hosts under fermentation conditions. For illustration, examples of preferred promoters are given as follows:

Bacteria (e.g. *Escherichia coli*): lac, tac, trp, tet, T3 T7, CP7, CP21, araBAD Yeast (e.g. *Pichia, Saccharomyces*): AOXI, AOXII, FMDH, GAP, TEF, PFK1, FBA1, PGK1, ADH1, ADH2, TDH3

Fungi (e.g. *Trichoderma*): CBHI, CBHII, EGI, PGK, BGL, XYL1, XYL2

Further examples of suitable promoters for heterologous expression are reported in the literature. Other parts of the expression construct are genetic elements requirements for a stable heritage of the introduced nucleic acids and selectable markers including genetic elements referring antibiotic resistance or complementing defined auxotrophies of the host strain.

The sequence of all nucleic acids of the invention, or of nucleic acids encoding polypeptides/proteins of the invention can be adjusted towards optimal codon usage in the selected expression host. The nucleic acids having such optimized/optimal codon usage for the particular expression host are also part of this invention. A production host is used herein synonymously to expression host and means an organism, which, upon cultivation produces the protein of the present invention. In one embodiment, the protein of the present invention is not secreted by the production host; however, in a preferred embodiment, it is secrested into the surrounding medium. Such an organisms is preferably selected from the kingdom of Bacteria, Archea, Yeasts, Fungi, and/or Plants. One preferred expression host is *Pichia pastoris*.

"Bacteria" shall herein refer to prokaryotic organisms. In a preferred embodiment Bacteria are eubacteria, and even more preferably they are selected among of the genus *Escherichia, Bacillus, Klebsiella, Streptomyces, Lactococcus* and *Lactobacillus* in particular *Escherichia coli, Bacillus subtilis, Bacillus licheniformis, Bacillus amyloliquefaciens, Bacillus megaterium, Klebsiella planticola, Streptomyces lividans, Lactococcus lactis, Lactobacillus brevis*.

"Yeast" shall herein refer to all lower eukaryotic organisms showing a unicellular vegetative state in their life cycle. This especially includes organisms of the class Saccharomycetes, in particular of the genus *Saccharomyces, Pachysolen, Pichia, Candida, Yarrowina, Debaromyces, Klyveromyces, Zygosaccharomyces*.

"Filamentous fungi" or "fungi" shall herein refer to all lower eukaryotic organisms showing hyphal growth during at least one state in their life cycle. This especially includes organisms of the phylum Ascomycota and Basidiomycota, in particular of the genus *Trichoderma, Talaromyces, Aspergillus, Penicillium, Chrysosporium, Phanerochaete, Thermoascus, Agaricus, Pleutrus, Irpex*.

"Plant" shall herein refer to all eukaryotic organisms belonging to the kingdom of plants. In a preferred embodiment the expression host is selected form plants of the genus *Zea, Triticum, Hordeum, Secale, Miscanthus, Saccharum, Solanum, Ipomea, Manihot, Helianthus, Camellia, Aspalathus, Eucalyptus, Beta, Fagus*, members of the family of Pinaceae, Betulaceae, Malvaceae, Cupressaceae, Rosaceae, Arecaceae.

Enzyme formulation is meant to be any liquid or solid composition containing the enzyme as a fraction. Additional components preferably comprise water, polyols, sugars, detergents, buffering agents, reducing agents, inorganic salts, solid carriers, conserving agents especially with antibacterial or anti-fungal activity, dyes, fragrances and/or perfumes.

Uses of endoglucanases, such as particularly of the endoglucanase of the present invention (non-limiting examples): hydrolysis of lignocellulose feedstocks for the generation of monomeric, dimeric or or oligomeric sugars; production of pulp and paper; textile applications for the improvement or general processing of fibers, yarns or denim; cleaning applications for industrial or home care applications; release of nutrients, production yield enhancement or improvement of dough properties in the field of food and feed.

DETAILED DESCRIPTION OF THE INVENTION

The invention relates to GH7 endoglucanases with superior properties. More particularly, the invention relates to thermostable endoglucanase proteins (polypeptides). The solutions provided are:

1. A protein having endoglucanase activity which belongs to the GH7 class and which shows active thermostabilization.
2. A protein having endoglucanase activity which comprises an amino acid sequence having at least 96%, preferably at least 97%, more preferably at least 98%, even more preferably at least 99%, such as at least 99.5% identity to SEQ. ID NO.: 2.

These two embodiments are described in detail below.

The temperature stability is defined above. An example for the determination of the thermostability is given in Example 4. Endoglucanases of the GH7 class are listed in the Table 1 (EC 3.2.1.4). Unless excluded by particular sequence identity constraints in a particular claim, the invention relates to variants of all endoglucanases of the GH7 class, comprised therein variants of the ones shown in Table 1.

TABLE 1

Known endoglucanases of the GH7 class

| | Protein Name | Organism | GenBank | PDB/3D |
|---|---|---|---|---|
| 1 | cellulase III-A (peptide fragment) | *Acremonium cellulolyticus* | | |
| 2 | endo-β-1,4-glucanase (EglB; AN3418.2) | *Aspergillus nidulans* FGSC A4 | EAA63386.1 | |
| 3 | endo-β-1,4-glucanase (CelB) | *Aspergillus oryzae* KBN616 | BAA22589.1 | |
| 4 | endo-β-1,4-glucanase (CelB; AO090010000314) | *Aspergillus oryzae* RIB40 | AEB00821.1 | |
| 5 | endo-β-1,4-glucanase I | *Aspergillus terreus* MS-31 | ADR78837.1 | |
| 6 | endo-β-1,3-1,4-glucanase (Bgl7A) | *Bispora* sp. MEY-1/CGMCC 2500 | ACT53749.1 | |
| 7 | EG I (peptide fragment) (Cel7C) | *Chrysosporium lucknowense* | | |
| 8 | endo-β-1,4-glucanase (CLhgEG1) | *Coptotermes lacteus* symbiont WH2002 | BAC07551.1 | |
| 9 | endo-β-1,4-glucanase (CLhgEG2) | *Coptotermes lacteus* symbiont WH2002 | BAC07552.1 | |
| 10 | endo-β-1,4-glucanase (EglB) | *Emericella nidulans* | AAM54071.1 | |
| 11 | endo-β-1,4-glucanase I (EG I; Eg1; Fof7) (Cel7B) | *Fusarium oxysporum* | AAA65586.1 | 1OVW [A, B, C, D] |
| 12 | endoglucanase 3 (HmEG3) (fragment) | *Holomastigotoides mirabile* | BAB64565.1 | |
| 13 | endoglucanase 2 (HmEG2) | *Holomastigotoides mirabile* | BAB64564.1 | |
| 14 | endoglucanase 1 (HmEG1) | *Holomastigotoides mirabile* | BAB64563.1 | |
| 15 | endo-β-1,4-glucanase I (Egl1; EG-I) | *Humicola grisea* var. *thermoidea* | BAA09786.1 | |
| 16 | endoglucanase 1 (EG I; EG1) (Cel7B) | *Humicola insolens* | AAE25068.1 | 1A39 [A] |
| 17 | endo-β-1,4-glucanase I (EGI; Egl1; EG-I) (Cel7B) | *Hypocrea jecorina* | AAA34212.1 | 1EG1 [A, C] |
| 18 | endoglucanase I (Egl) | *Hypocrea jecorina* M5 | ADM08177.1 | |
| 19 | endo-β-1,4-glucanase (Egl1) | *Hypocrea jecorina* PTCC 5142 | AAX28897.1 | |
| 20 | endoglucanase I | *Hypocrea pseudokoningii* | ABM90986.1 | |
| 21 | endoglucanase I (Eg1) | *Hypocrea pseudokoningii* 3.3002 | AEQ29501.1 | |
| 22 | endoglucanase I (Eg1) | *Hypocrea rufa* | AEOI7039.1 | |
| 23 | endo-β-1,4-glucanase I (EGI; BglI) | *Hypocrea rufa* AS 3.3711 | AAQ21382.1 | |
| 24 | endoglucanase I | *Hypocrea rufa* HK-75 | | |
| 25 | endo-β-1,4-glucanase (Egl1; MG02532.4) | *Magnaporthe grisea* 70-15 | XP_366456.1 | |
| 26 | endoglucanase | *Myceliophthora thermophila* CBS 117.65 | AAE25067.1 | |
| 27 | endoglucanase I (Egl1) (Cel7B) | *Penicillium decumbens* 114-2 | ABY56790.1 | |
| 28 | endoglucanase I (Egl1) | *Penicillium decumbens* L-06 | ACJ15337.1 | |
| 29 | endoglucanase I (Egl1; Eg1) | *Penicillium oxalicum* | ACS32299.1 | |
| 30 | endoglucanase (Cel7B) | *Penicillium purpurogenum* | AEL78899.1 | |
| 31 | endoglucanase (Bgl7C7) | *Penicillium* sp. C7 | AEG74551.1 | |
| 32 | endo-β-1,4-glucanase (EGI) (peptide fragments) (Cel7B) | *Peniciliium verruculosum* | | |
| 33 | endoglucanase 3 (PgEG3) | *Pseudotrichonympha grassii* | BAB64562.1 | |
| 34 | endoglucanase 2 (PgEG2) | *Pseudotrichonympha grassii* | BAB64561.1 | |
| 35 | endoglucanase 1 (PgEG1h) | *Pseudotrichonympha grassii* | BAB64553.1 | |

TABLE 1-continued

Known endoglucanases of the GH7 class

| | Protein Name | Organism | GenBank | PDB/3D |
|---|---|---|---|---|
| 36 | Egl1 (fragment) | *Trichoderma asperellum* T203 | AAS37698.1 | |
| 37 | endoglucanase I | *Trichoderma longibrachiatum* 3.1029 | AEI71804.1 | |
| 38 | endoglucanase I (Egl1) | *Trichoderma longibrachiatum* 36MS | AEC03714.1 | |
| 39 | endo-β-1,4-glucanase I (Egl1; EglI; TlCel7A) (Cel7A) | *Trichoderma longibrachiatum* CECT 2606 | 1920181A | |
| 40 | endoglucanase I | *Trichoderma longibrachiatum* FU05 | ACZ34302.1 | |
| 41 | endoglucanase I (Egl; EGI) | *Trichoderma* sp. SSL | ACH68455.1 | |
| 42 | endo-β-1,4-glucanase (RsSymEG1; SM2038B11) | uncultured symbiotic protist of *Reticulitermes speratus* | BAF57296.1 | |

The first and second aspects will now be described in detail.

First Aspect: A Protein Having Endoglucanase Activity which Belongs to the GH7 Class and which Shows Active Thermostabilization.

In the first aspect of the invention the proteins have endoglucanase activity and superior thermal properties. The superior thermal properties are defined as a temperature stability that manifests in a relative substrate conversion activity higher than 90% (such as higher than 95%) upon incubation at temperatures of 60° C. or higher, and active thermostabilization. The active thermostabilization is described in the following.

The inventors of the present invention have surprisingly found out that proteins showing active thermostabilization also show temperature stability.

This was shown by the following example. The inventors generated a GH7 endoglucanase, that is a particular variant of SEQ ID NO: 4 (i.e. the one given by SEQ ID NO: 2) as follows. A nucleic acid encoding a polypeptide with SEQ ID NO: 2 was obtained by random mutagenesis (error prone PCR, as described in Example 1). Methods for random mutagenesis are well known in the art. Furthermore, now that the inventors have disclosed here the suitability of a polypeptide encoded by SEQ ID NO: 2, a respective nucleic acid encoding this protein can be directly prepared by the skilled person. Methods therefor include for example gene synthesis or site-directed mutagenesis, starting from a nucleic acid with a high degree of sequence identity (e.g. more than 90%) to SEQ ID NO: 4 and introduction of mutations by site-directed mutagenesis (in one or several steps) to obtain the nucleic acid encoding the protein of SEQ ID NO: 2. A starting sequence from which the nucleic acid encoding SEQ ID NO. 2 can be obtained by mutagenesis is Cel7B from *Hypocrea pseudokonigii* given here as SEQ ID NO: 4 (Gene Bank Accession number ABM90986).

Figure 3:
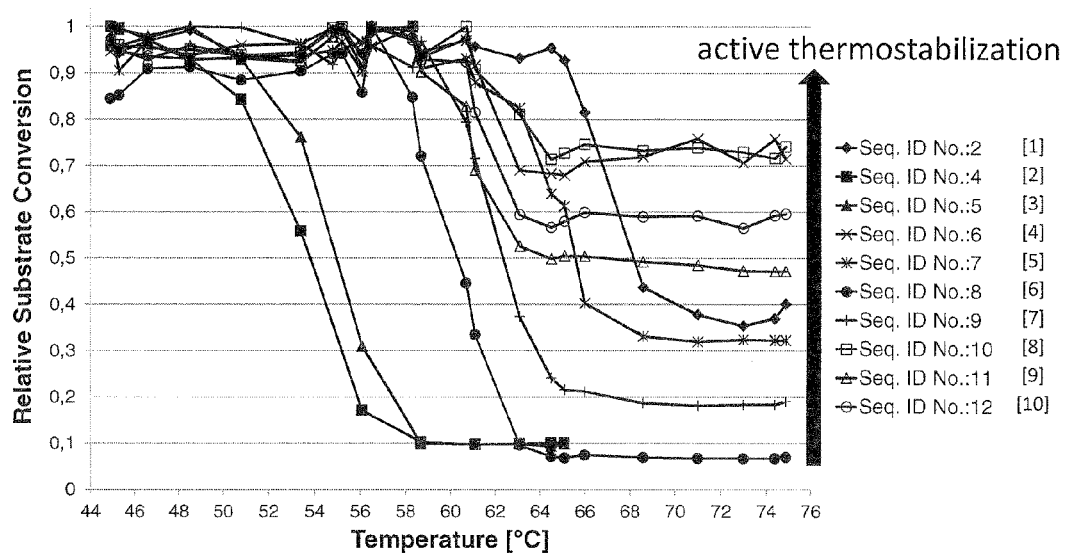
FIG. 3: Endoglucanase variants showing increased temperature stability ([6] and [3]) and variants with increased temperature stability and active thermostabilization [1], [4], [5], [7], [8], [9] and [10] in comparison to a native GH7 protein [2].
Figure 4:
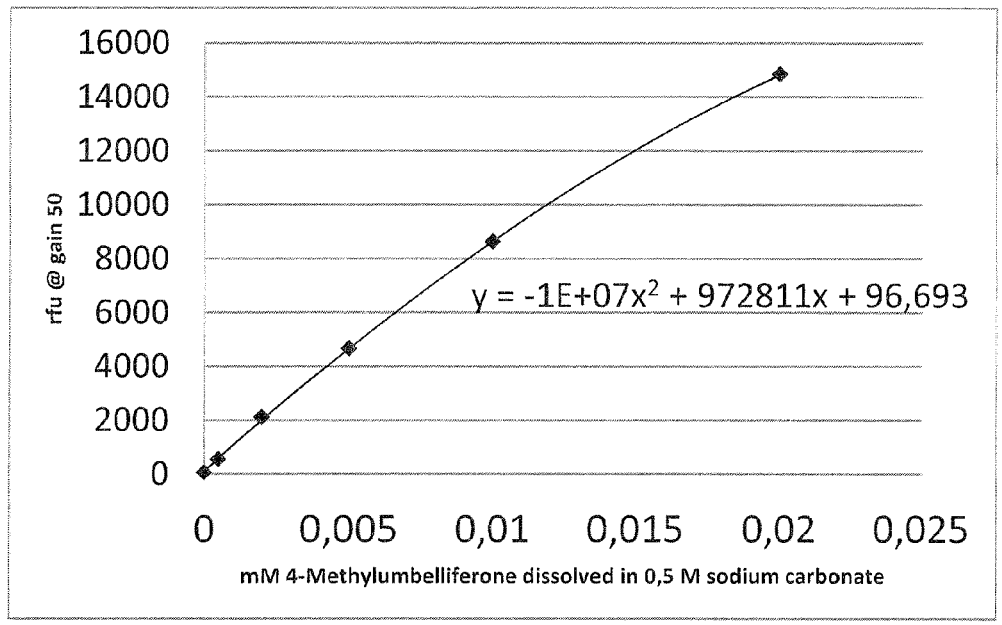
FIG. 4: Calibration of 200 μl portions of alkaline 4-methylumbelliferone solution to the fluorescence read out in a Tecan Infinite M200 plate-reader. A 10 mM solution was prepared by dissolving 440 mg of 4-methyl umbelliferone (Sigma Aldrich Cat. Nr. 69580) in 250 ml of 0.5 M sodium carbonate solution. Serial dilutions were prepared by in 0.5 M sodium carbonate. Fluorescence intensity was measured at 360 nm/454 nm with at gain 50.

The inventors of the present invention characterized the thermostability of the protein having SEQ ID NO: 2. As can be seen in FIG. 3, this protein solves the technical problem underlying the present invention, i.e. has higher temperature stability than its parental protein (SEQ ID NO: 4). This is evident for example from the fact that the relative substrate conversion is still near its maximum at e.g. 60° C., whereas the relative substrate conversion of the protein having SEQ ID NO: 4 is at a very low level at said temperature (see FIG. 3).

Surprisingly, the inventors have found that at even higher temperatures, e.g. in the range from 68 to 76° C. (including 70 to 74° C.), the relative substrate conversion does not significantly drop with increasing temperature. This is in sharp contrast to the properties of the parental protein having SEQ ID NO: 4, which, in a plot against increasing temperatures, shows a decrease of relative substrate conversion, the decrease going down to background levels without any intermediate plateau. It is believed that the protein having SEQ ID NO: 4, when exposed to higher temperatures, e.g. 60° C. or more, such as 70° C. or more, is not present in its active state. Without wishing to be bound to any particular theory, it is believed that this effect is due to thermal unfolding (or folding of non-active conformations) of the protein. Without wishing to be bound to any particular theory, the effect of activity loss at high temperatures will in the following be called thermal unfolding. Thermal unfolding is a well-known phenomenon for proteins of almost any type, particularly enzymes, at higher temperatures. The thermal unfolding observed for the protein having SEQ ID NO: 4 is thus in line with the expectations of a skilled person. The protein of SEQ ID NO: 4 is not part of the invention.

In sharp contrast, the protein of this aspect of the invention shows a plateau phase at higher temperatures, e.g. in the range from 68 to 76° C. (including 70 to 74° C.). This plateau is lower than the maximum relative substrate conversion, but higher than the background relative substrate conversion. Without wishing to be bound to any particular theory, the inventors of the present invention conclude that the protein of the invention is present at these higher temperatures in a state which is different from the folded state at lower temperatures (e.g. 46° C.), but yet this protein is enzymatically active. It may thus be assumed that at high temperatures, this protein of the invention actively refolds, i.e. refolds to obtain a further active state (and thus enabling the observed relative substrate conversion at higher temperatures). The inventors have therefore termed this property, which is also defined above in the definitions section, as "active thermostabilization".

The protein of the invention thus solves the technical problem underlying the present invention by being temperature stable. Furthermore, based on the disclosure of the present invention, the skilled worker is given guidance for the identification of further proteins according to this first aspect of the invention.

Such further proteins may be found as follows. First, any type of mutations (including deletion, insertion or replacement of one or several amino acid residues, and being randomly or directed) may be introduced into any endoglucanase of the GH7 family, particularly into any one named in Table 1 to obtain a mutant protein, or a library thereof. The, the so-obtained mutant protein or the library thereof may be screened for active thermostabilization as defined above. The known proteins given in table 1 above are not part of the invention, but any mutants thereof showing active thermostabilization are included in the invention.

Importantly, all enzymes of the first aspect of the present invention, i.e. the ones which show active thermostabilization as defined above, show temperature stability as defined above. The active thermostabilization is thus, in a first aspect, a solution to the problem underlying the present invention. Whether or not any given protein falls under the first aspect of the invention can be reliably tested by the assay for active thermostabilization given above.

Second Aspect: A Protein Having Endoglucanase Activity which Comprises an Amino Acid Sequence Having at Least 96%, Preferably at Least 97%, More Preferably at Least 98%, Even More Preferably at Least 99%, Such as at Least 99.5% Identity to SEQ. ID NO.: 2.

In searching a second solution to the problem underlying the present invention, the inventors embarked on a mutagenesis project, starting from the protein of SEQ ID NO: 2. Thus, the inventors have introduced mutations, such as point mutations, into the protein having SEQ ID NO: 2 (i.e. by modifying the underlying nucleic acid, as described below). The inventors have found out that many such mutants also show temperature stability and thus solve the underlying problem in a second aspect. Examples of the solutions are given in FIG. 3.

Thus, in a second aspect, the invention relates to a protein having endoglucanase activity which comprises an amino acid sequence having at least 96%, preferably at least 97%, more preferably at least 98%, even more preferably at least 99%, such as at least 99.5% identity to SEQ. ID NO.: 2. This protein may typically belong to the GH7 class.

Particularly, the present invention also provides specific mutants of the protein with sequence of SEQ ID NO: 2. Thus, the sequence given in SEQ ID NO: 2 is modified in one or more (preferably 1, 2, 3, 4, 5, 6, 7, 8, 9, 10, 11, 12, 13, 14, 15, 16, 17, 18 or 19) positions. Such modification may consist of replacement, deletion, insertion and the like. In a particular embodiment thereof, the modification consists in a replacement. In an even more specific embodiment, the modification consists in a replacement of any one or more of the specific positions of SEQ ID NO: 2 which are individualized in the very left column of Tables 2, 3, 4.

While such modification at any of these given positions my in principle be a replacement by any amino acid residue, it is preferred that the replacement is a replacement by an amino acid residue given in lane number 4 of any one or more of Tables 2, 3 or 4, or by a an amino acid residue similar thereto (similar mutation as defined above). Thus, similar mutations as defined above might be introduced instead of the listed ones. Example 5 shows some of such mutants. Methods for the introduction of mutations are known in the art. Exemplary guidance can be taken from Example 1. In other words, a preferred embodiment of the invention relates to preferred positions for mutagenesis of endoglucanases of the GH7 class. A list of preferred exchanges is given in the Table 2, lane 2. In another preferred embodiment the preferred mutations are selected from the listing in Table 3, lane 2. In another preferred embodiment of the invention the preferred mutations are selected from Table 4, lane 2. It is also possible to combine two or three of these preferred embodiments, for example one or more preferred exchange given in Table 2 can be combined with one or more preferred exchanges given in Table 3 and/or Table 4.

TABLE 2

Preferred exchanges of Amino acids with respect to Seq. ID NO. 2

| Position of Seq. ID NO: 2 | Amino Acid at Position in Seq. ID NO: 2 lane 1 | Preferred Amino acids in GH7 endoglocanases by ClustalW alignment to Seq. ID NO: 2 lane 2 | Most preferred Amino acids in GH7 endoglocanases by ClustalW alignment to Seq. ID NO: 2 lane 3 | alternative amino acid exchanges for Seq. ID NO: 2 lane 4 |
|---|---|---|---|---|
| 2 | L | L, Q | L, Q | Q |
| 8 | T | T, C | T | |
| 16 | T | T, C | T | |
| 19 | K | K, E | K | |
| 23 | S | S, H | S, H | H |
| 30 | N | N, D | N | |
| 32 | Y | Y, S | Y, S | S |
| 41 | W | W, R | W | |
| 42 | I | I, M | I, M | M |
| 48 | N | N, Y | N | |
| 55 | G | G, C | G, C | C |
| 64 | E | E, H, K | E, H, K | H, K |
| 65 | A | A, D | A, D | D |
| 67 | G | G, C | G, C | C |
| 68 | S | S, C, G | S, C, G | C, G |
| 75 | G | G, C | G | |
| 86 | N | N, S | N, S | S |
| 88 | S | S, C, D, F, T | S, D | D |
| 93 | N | N, H, R, Y | N, H, R | H, R |
| 104 | I | T, S | T, S | S |
| 107 | S | S, T | S | |
| 118 | K | K, E | K | |
| 137 | A | A, D | A, D | D |
| 144 | A | A, G | A | |
| 145 | S | S, A | S | |
| 150 | Q | Q, E | Q, E | E |
| 153 | E | E, K | E | |

TABLE 2-continued

Preferred exchanges of Amino acids with respect to Seq. ID NO. 2

| Position of Seq. ID NO: 2 | Amino Acid at Position in Seq. ID NO: 2 lane 1 | Preferred Amino acids in GH7 endoglocanases by ClustalW alignment to Seq. ID NO: 2 lane 2 | Most preferred Amino acids in GH7 endoglocanases by ClustalW alignment to Seq. ID NO: 2 lane 3 | alternative amino acid exchanges for Seq. ID NO: 2 lane 4 |
|---|---|---|---|---|
| 164 | G | G, S | G | |
| 179 | Q | Q, L | Q | |
| 185 | T | T, D, E | T, D, E | D, E |
| 191 | Q | Q, K | Q, K | K |
| 193 | F | F, S | F | |
| 201 | L | L, F | L, F | F |
| 210 | L | L, M, Y | L, M | M |
| 212 | P | P, L, S | P | |
| 216 | N | N, T | N | |
| 217 | A | A, Y | A | |
| 231 | R | R, G, H, K | R, H, K | H, K |
| 233 | G | G, N | G | |
| 235 | P | P, S | P | |
| 242 | G | G, D | G | |
| 249 | P | P, R | P, R | R |
| 261 | G | G, C | G | |
| 263 | P | P, T | P, T | T |
| 271 | T | T, K | T, K | K |
| 277 | N | N, D, E | N, D, E | D, E |
| 290 | T | T, E | T, E | E |
| 293 | S | S, T | S | |
| 299 | T | T, A | T, E | E |
| 312 | E | E, D, S | E, D, S | D, S |
| 317 | I | I, V | I | |
| 322 | N | N, W | N | |
| 323 | D | D, N | D | |
| 325 | S | S, T | S | |
| 327 | Y | Y, F | Y | |
| 328 | M | M, K | M | |
| 335 | D | D, E, S | D, E, S | E, S |
| 352 | N | N, V, W | N | |
| 357 | H | H, E | H, E | E |
| 360 | Y | Y, F | Y | |
| 379 | P | P, L | P, L | L |
| 382 | P | P, del | P | |
| 383 | P | P, del | P | |
| 390 | S | S, L | S | |
| 391 | T | T, I | T, I | I |
| 392 | A | A, T | A, T | T |
| 398 | S | S, T | S, T | T |
| 405 | I | I, T | I, T | T |
| 431 | Y | Y, H | H | |
| 432 | S | S, G | S, G | G |
| 434 | D | D, Y | D, Y | Y |
| 448 | H | H, Y | H | |

TABLE 3

Preferred exchanges of Amino acids with respect to Seq. ID NO. 2

| Position of Seq. ID NO: 2 | Amino acid at Position in Seq. ID NO: 2 lane 1 | Preferred Amino acids in GH7 endoglocanases by ClustalW alignment to Seq. ID NO: 2 lane 2 | Most preferred Amino acids in GH7 endoglocanases by ClustalW alignment to Seq. ID NO: 2 lane 3 | alternative amino acid exchanges for Seq. ID NO: 2 lane 4 |
|---|---|---|---|---|
| 23 | S | S, H | S, H | H |
| 30 | N | N, D | N | |
| 41 | W | W, R | W | |
| 55 | G | G, C | G, C | C |
| 64 | E | E, H, K | E, H, K | H, K |
| 65 | A | A, D | A, D | D |
| 67 | G | G, C | G, C | C |
| 118 | K | K, E | K | |
| 137 | A | A, D | A, D | D |
| 144 | A | A, G | A | |
| 150 | Q | Q, E | Q, E | E |
| 164 | G | G, S | G | |
| 179 | Q | Q, L | Q | |
| 185 | T | T, D, E | T, D, E | D, E |

TABLE 3-continued

Preferred exchanges of Amino acids with respect to Seq. ID NO. 2

| Position of Seq. ID NO: 2 | Amino acid at Position in Seq. ID NO: 2 lane 1 | Preferred Amino acids in GH7 endoglocanases by ClustalW alignment to Seq. ID NO: 2 lane 2 | Most preferred Amino acids in GH7 endoglocanases by ClustalW alignment to Seq. ID NO: 2 lane 3 | alternative amino acid exchanges for Seq. ID NO: 2 lane 4 |
|---|---|---|---|---|
| 191 | Q | Q, K | Q, K | K |
| 201 | L | L, F | L, F | F |
| 212 | P | P, L, S | P | |
| 216 | N | N, T | N | |
| 231 | R | R, G, H, K | R, H, K | H, K |
| 242 | G | G, D | G | |
| 249 | P | P, R | P, R | R |
| 261 | G | G, C | G | |
| 263 | P | P, T | P, T | T |
| 271 | T | T, K | T, K | K |
| 277 | N | N, D, E | N, D, E | D, E |
| 290 | T | T, E | T, E | E |
| 299 | T | T, A | T, E | E |
| 312 | E | E, D, S | E, D, S | D, S |
| 323 | D | D, N | D | |
| 325 | S | S, T | S | |
| 328 | M | M, K | M | |
| 335 | D | D, E, S | D, E, S | E, S |
| 357 | H | H, E | H, E | E |
| 379 | P | P, L | P, L | L |
| 390 | S | S, L | S | |
| 391 | T | T, I | T, I | I |
| 405 | I | I, T | I, T | T |
| 432 | S | S, G | S, G | G |
| 434 | D | D, Y | D, Y | Y |

TABLE 4

Preferred exchanges of Amino acids with respect to Seq. ID NO. 2

| Position of Seq. ID NO: 2 | Amino acid at Position in Seq. ID NO: 2 lane 1 | Preferred Amino acids in GH7 endoglocanases by ClustalW alignment to Seq. ID NO: 2 lane 2 | GH7 endoglocanases by ClustalW alignment to Seq. ID NO: 2 lane 3 | alternative amino acid exchanges for Seq. ID NO: 2 lane 4 |
|---|---|---|---|---|
| 2 | L | L, Q | L, Q | Q |
| 8 | T | T, C | T | |
| 16 | T | T, C | T, C | C |
| 19 | K | K, E | K | |
| 32 | Y | Y, S | Y, S | S |
| 42 | I | I, M | I, M | M |
| 48 | N | N, Y | N | |
| 68 | S | S, G | S, G | G |
| 75 | G | G, C | G | |
| 86 | N | N, S | N, S | S |
| 88 | S | S, C, D, F, T | S, C | C |
| 93 | N | N, H, R, Y | N | |
| 104 | T | T, S | T, S | S |
| 107 | S | S, T | S | |
| 145 | S | S, A | S | |
| 153 | E | E, K | E | |
| 193 | F | F, S | F | |
| 210 | L | L, M, Y | L | |
| 217 | A | A, Y | A | |
| 233 | G | G, N | G | |
| 235 | P | P, S | P | |
| 293 | S | S, T | S | |
| 317 | I | I, V | I | |
| 322 | N | N, W | N | |
| 327 | Y | Y, F | Y | |
| 352 | N | N, V, W | N, V | V |
| 360 | Y | Y, F | Y | |
| 382 | P | P, del | P | |
| 383 | P | P, del | P | |
| 392 | A | A, T | A, T | T |
| 398 | S | S, T | S, T | T |
| 431 | Y | Y, H | H | |
| 448 | H | H, Y | H | |

The first and second aspect of the invention, although being different solutions to the same problem, are not necessarily mutually exclusive. Thus, the invention relates to proteins fulfilling the conditions of both the first aspect and the second aspect above. It is important to note that the first aspect and the second aspect are two alternative solutions to the problem of providing GH7 enzymes with improved temperature stability. These solutions are independent (although for some examples overlapping) and thus need not be necessarily combined. For example, the protein identified as [6] in FIG. 3 shows temperature stability compared to the protein having SEQ ID NO: 4 ([2] in FIG. 3), yet does not display active thermostabilization.

The invention thus provide may different enzyme variant according to the first aspect above and/or according to the second aspect above. Whether any given enzyme shows the desired thermal properties (temperature stability and/or active thermostabilization) can be easily tested by the test entitled "Determination of thermostability and/or active thermostabilization" above.

As given in detail above in the definitions section, as well as individualized by the examples below, it is briefly summarized here how the desired mutations can be obtained:

Pairwise alignment of any GH7 endoglucanase sequence with Seq ID NO 2 using the ClustalW algorithm Identification of corresponding positions (lane 1) in the GH7 endoglucanase target sequence Modification of corresponding positions in the GH7 endoglucanase target sequence according to the proposed preferred exchanges given in lane 2, or preferably in lane 3

Expression of the modified sequence and testing of the expressed protein for improved thermal properties It is believed that the thermostable enzymes of the invention also come with reduced of agglomerate formation at higher temperatures, and thus with reduced precipitation. The avoidance of such precipitates is particularly advantageous in the presence of garnets, denim or woven materials as well for the application in membrane reactors, reducing the membrane fouling characteristics.

Fusion proteins comprising any protein of the invention are also part of the invention.

Another aspect of the invention is related to the production of the proteins of the invention by heterologous expression in a production host, also termed expression host. Methods for the heterologous expression comprise the transfer of a nucleic acid encoding the protein of the invention (expression construct) into the production host by transformation, transfection, crossing or equivalent methods with respect to the nucleic acid (DNA or RNA) transfer. Methods for transformation within the meaning of this invention are not particularly limited. Examples have been reported for a variety of species and include electroporation, protoplast-transformation, chemical transformation, and transfer via ballistic particles, micro-injection, viral-infection, crossing mating or the use of natural competent strains or cell lines. A preferred production host co-secretes the endoglucanase of the invention with other cellulases, hemi-cellulases or pectinases into the culture broth. It is thus preferred that the coding sequence on the expression construct encodes for the endoglucanase of the invention preceded by a signal for secretion from the particular host strain. Such signals are well known in the art; for example in Eubacteria they are called signal peptides. Without wishing to be bound to a particular theory, these signals have in common the ability to direct secretion of a protein, typically in a co-translational fashion. A preferred expression host is *Trichoderma reesei*.

A further aspect of the invention is the application of the above-described endoglucanase proteins. This includes the applications of the purified, partially purified ore crude protein preparations as such or in enzyme formulation, as well as the application of whole cells or organisms, expressing the target protein. Fields of applications for endoglucanases can be found in the chapter field of invention. As stated there the application of thermal stable proteins is highly desirable. A preferred application of the endoglucanase lies in the field of enzymatic lignocellulose conversion.

Overview of the Sequences Disclosed Herein

| Seq. ID NO | Type | Function | Source |
|---|---|---|---|
| 1 | DNA | DNA sequence encoding Seq. ID NO: 2 (GH7 endoglucanase of the invention)-adapted codon usage for *Pichia pastoris* | Artificial |
| 2 | Protein | GH7 endoglucanase of the invention-mature protein sequence | Artificial |
| 3 | DNA | DNA sequence encoding Seq. ID NO: 4 (GH7 endoglucanase Cel7B DNA)-adapted codon usage | Artificial |
| 4 | Protein | Endoglucanase I (Cel7B)-mature protein sequence | *Hypocrea pseudokonigii*-ABM90986 |
| 5 | Protein | Endoglucanase I (Cel7B)-mature protein sequence | Artificial |
| 6 | Protein | GH7 endoglucanase of the invention-mature protein sequence | Artificial |
| 7 | Protein | GH7 endoglucanase of the invention-mature protein sequence | Artificial |
| 8 | Protein | Endoglucanase I (Cel7B)-variant of the mature protein sequence | Artificial |
| 9 | Protein | GH7 endoglucanase of the invention-mature protein sequence | Artificial |
| 10 | Protein | GH7 endoglucanase of the invention-mature protein sequence | Artificial |
| 11 | Protein | GH7 endoglucanase of the invention-mature protein sequence | Artificial |
| 12 | Protein | GH7 endoglucanase of the invention-mature protein sequence | Artificial |
| 13 | Protein | Endoglucanase I (Cel7B)-variant of the mature protein sequence | Artificial |
| 14 | Protein | Endoglucanase I (Cel7B)-variant of the mature protein sequence | Artificial |
| 15 | DNA | DNA sequence coding for expression of Seq. ID NO. 2 with N-terminal 6x Histidine TAG (*italic*) with $SP_{mfa}$ signal peptide (underlined) in *pichia pastoris* | Artificial |
| 16 | DNA | DNA sequence coding for Seq. ID NO. 2 in fusion with CBHI signal peptide (underlined) for expression in *Trichoderma reesei* | Artificial |

Sequences Disclosed Herein (NO: 1-16)

SEQ ID NO: 1
TCTCTGCAGCCAGGAACTTCTACTCCAGAGGTGCACCCAAAGCTGAC-
CACCT

ACAAGTGTACCACCTCTGGTGGTTGTGTTGCTCAGAACACCTATGTTGT-
TCT

GGACTGGAACTACAGATGGATCGACGACGCCAACTACAACTCTTGTAC-
CGTG

AACGGTGGTGTCAACACTACTCTGTGTCCAGACGAGGCTACTGGTAG-
CAAGA

ACTGCTTCATCGAGGGTGTTGACTACGCTGCTTCTGGTGTTACTGC-
CAATGG

TTCTACCTTGACCCTGAACCAGTACATGCCATCTTCCTCTGGCGGTTA-
CACT

TCTGTGTCGCCAAGACTGTACTTGTTGGGTCCAGACGGTAAGTACGT-
TATGC

TGAAGCTGAACGGACAGGAGCTGTCTTTTGACGTTGACCTGTCTGCTTT-
GCC

ATGTGGAGAGAACGCTTCTCTGTACCTGTCTCAGATGGACGAGAACG-
GTGGA

GCTAACCAGTACAACACCGCCGGTGCTAACTACGGTTCTGGTTACTGT-
GACG

CCCAGTGTCCAGTTCAGACTTGGAGAAACGGAACCCTGAACACTTCTG-
GCCA

GGGATTCTGCTGTAACGAGATGGACATCTTGGAGGGAAACTCTA-
GAGCTAAC

GCTCTGACCCCACACTCTTGTAATGCTACCGCTTGTGACTCTGCTGGTT-
GCG

GTTTTAACCCATACCGCTCGGGTTACCCAAACTACTTTGGCCCAGGTG-
GCAC

TGTTGACACCTCGAAGCCATTCACCATCATCACCCAGTTCAACACCGA-
CAAC

GGTTCTCCATCTGGTAACCTGGTGTCGATCACCAGAAAGTACAGACA-
GAACG

GCGTTGACATCCCATCTGCTAAACCAGGTGGCGACACCATTTCGTCTT-
GTCC

ATCTGCCTCTACTTACGGTGGATTGGCTACCATGGGAAAGGCTCTGTC-
CGAG

GGAATGGTGCTGATCTTCTCGATCTGGAACGACAACTCGCAGTACAT-
GAACT

GGCTGGACTCTGGTGATGCTGGTCCATGTTCTTCTACCGAGGGCAAC-
CCATC

TAACATCCTGGCTAACAACCCTGGTACTCACGTGGTGTACTC-
GAACATTAGA

TGGGGCGACATTGGTTCTACCACCAACTCTACCGGTGGTAACCCACCAC-
CAC

CACCTGCATCTTCTACCACCTTCTCGACCGCCAGAAGATCGTCTACCTC-
CTC

TTCTTCTCCATCTTGTATCCAGACTCACTGGGGTCAGTGTGGTGGTAT-
TGGC

TACACCGGCTGTAAGACCTGTACCTCTGGAACCACTTGCCAGTACAG-
CAACG

ACTACTACTCTCAGTGCCTGTGA

SEQ ID NO: 2
SLQPGTSTPEVHPKLTTYKCTTSGGCVAQNTYVVLDWNYRWIHDANYN-
SCTV

NGGVNTTLCPDEATGSKNCFIEGVDYAASGVTANGSTLTLN-
QYMPSSGGYT

SVSPRLYLLGPDGKYVMLKLNGQELSFDVDLSALPCGENASLYLSQM-
DENGG

ANQYNTAGANYGSGYCDAQCPVQTWRNGTLNTSGQGFCCNEMDILEGN-
SRAN

ALTPHSCNATACDSAGCGFNPYRSGYPNYFGPGGTVDTSKPFTIITQF-
NTDN

GSPSGNLVSITRKYRQNGVDIPSAKPGGDTISSCPSASTYGGLATMG-
KALSE

GMVLIFSIWNDNSQYMNWLDSGDAGPCSSTEGNPSNILANNPGTHVVYS-
NIR

WGDIGSTTNSTGGNPPPPPASSTTFSTARRSSTSSSSPSCIQTHWGQCG-
GIG

YTGCKTCTSGTTCQYSNDYYSQCL*

SEQ ID NO: 3
TCTCAGCAGCCAGGAACTTCTACTCCAGAGGTGCACCCAAAGCTGAC-
CACCT

ACAAGTGTACCACCTCTGGTGGTTGTGTTGCTCAGGACACCTCTGTTGT-
TCT

GGACTGGAACTACAGATGGATGCACGACGCCAACTACAACTCTTGTAC-
CGTG

AACGGTGGTGTCAACACTACTCTGTGTCCAGACGAGGCTACTTGTG-
GCAAGA

ACTGCTTCATCGAGGGTGTTGACTACGCTGCTTCTGGTGTTACTGC-
CTCTGG

TTCTACCTTGACCCTGAACCAGTACATGCCATCTTCCTCTGGCGGT-
TACTCT

TCTGTGTCGCCAAGACTGTACTTGTTGGGTCCAGACGGTGAGTACGT-
TATGC

TGAAGCTGAACGGACAGGAGCTGTCTTTTGACGTTGACCTGTCTGCTTT-
GCC

ATGTGGAGAGAACGGTTCTCTGTACCTGTCTCAGATGGACGAGAACG-
GTGGA

GCTAACCAGTACAACACCGCCGGTGCTAACTACGGTTCTGGTTACTGT-
GACG

CCCAGTGTCCAGTTCAGACTTGGAGAAACGGAACCCTGAACACTTCTG-
GCCA

GGGATTCTGCTGTAACGAGATGGACATCTTGGAGGGAAACTCTA-
GAGCTAAC

GCTCTGACCCCACACTCTTGTACTGCTACCGCTTGTGACTCTGCTGGTT-
GCG

GTTTTAACCCATACGGCTCGGGTTACCCAAACTACTTTGGCCCAGGT-
GACAC

TGTTGACACCTCGAAGCCATTCACCATCATCACCCAGTTCAACACCGA-
CAAC

GGTTCTCCATCTGGTAACCTGGTGTCGATCACCAGAAAGTACAGACA-
GAACG

GCGTTGACATCCCATCTGCTAAACCAGGTGGCGACACCATTTCGTCTT-
GTCC

ATCTGCCTCTGCTTACGGTGGATTGGCTACCATGGGAAAGGCTCTGTC-
CTCT

GGAATGGTGCTGATCTTCTCGATCTGGAACGACAACTCGCAGTACAT-
GAACT

GGCTGGACTCTGGTTCTGCTGGTCCATGTTCTTCTACCGAGGGCAAC-
CCATC

TAACATCCTGGCTAACAACCCTGGTACTCACGTGGTGTACTC-
GAACATTAGA

TGGGGCGACATTGGTTCTACCACCAACTCTACCGGTGGTAACCCACCAC-
CAC

CACCTGCATCTTCTACCACCTTCTCGACCACCAGAAGATCGTCTACCAC-
CTC

TTCTTCTCCATCTTGTACCCAGACTCACTGGGGTCAGTGTGGTGGTAT-
TGGC

TACACCGGCTGTAAGACCTGTACCTCTGGAACCACTTGCCAGTACG-
GCAACG

ACTACTACTCTCAGTGCCTGTGA

SEQ ID NO: 4
SQQPGTSTPEVHPKLTTYKCTTSGGCVAQDTSVVLDWNYRWMHDANYN-
SCTV

NGGVNTTLCPDEATCGKNCFIEGVDYAASGVTASGSTLTLN-
QYMPSSSGGYS

SVSPRLYLLGPDGEYVMLKLNGQELSFDVDLSALPCGENGSLYLSQM-
DENGG

ANQYNTAGANYGSGYCDAQCPVQTWRNGTLNTSGQGFCCNEMDILEGN-
SRAN

ALTPHSCTATACDSAGCGFNPYGSGYPNYFGPGDTVDTSKPFTIITQF-
NTDN

GSPSGNLVSITRKYRQNGVDIPSAKPGGDTISSCPSASAYGGLATMG-
KALSS

GMVLIFSIWNDNSQYMNWLDSGSAGPCSSTEGNPSNILANNPGTHVVYS-
NIR

WGDIGSTTNSTGGNPPPPPASSTTFSTTRRSSTTSSSPSCTQTHWGQCG-
GIG

YTGCKTCTSGTTCQYGNDYYSQCL*

SEQ ID NO: 5
SQQPGTSTPEVHPKLTTYKCTTSGGCVAQDTSVVLDWNYRWMHDANYN-
SCTV

NGGVNTTLCPDEATCGKNCFIEGVDYAASGVTASGSTLTLN-
QYMPSSSGGYS

SVSPRLYLLGPDGEYVMLKLNGQELSFDVDLSALPCGENGSLYLSQMD-
KNGG

ANQYNTAGANYGSGYCDAQCPVQTWRNGTLNTSGQGFCCNEMDILEGN-
SRAN

ALTPHSCTATACDSAGCGFNPYGSGYPNYFGPGDTVDTSKPFTIITQF-
NTDN

GSPSGNLVSITRKYRQNGVDIPSAKPGGDTISSCPSASAYGGLATMG-
KALSS

GMVLIFSIWNDNSQYMNWLDSGSAGPCSSTEGNPSNILANNPGTHVVYS-
NIR

WGDIGSTTNSTGGNPPPPPASSTTFSTTRRSSTTSSSPSCTQTHWGQCG-
GIC

YTGCKTCTSGTTCQYGNDYYSQCL*

SEQ ID NO: 6
SLQPGTSTPEVHPKLTTYKCTTSGGCVAQNTSVVLDWNYRWMHDANYN-
SCTV

NGGVNTTLCPDEATGGKNCFIEGVDYAASGVTASGSTLTLN-
QYMPSSSGGYS

SVSPRLYLLGPDGKYVMLKLNGQELSFDVDLSALPCGENASLYLSQM-
DENGG

ANQYNTAGANYGSGYCDAQCPVQTWRNGTLNTSGQGFCCNEMDILEGN-
SRAN

ALTPHSCNATACDSAGCGFNPYGSGYPNYFGPGGTVDTSKPFTIITQF-
NTDN

GSPSGNLVSITRKYRQNGVDIPSAKPGGDTISSCPSASTYGGLATMG-
KALSS

GMVLIFSIWNDNSQYMNWLDSGSAGPCSSTEGNPSNILANNPGTHVVYS-
NIR

WGDIGSTTNSTGGNPPPPPASSTTFSTTRRSSTSSSSPSCIQTHWGQCG-
GIG

YTGCKTCTSGTTCQYSNDYYSQCL*

SEQ ID NO: 7
SLQPGTSTPEVHPKLTTYKCTTSGGCVAQNTYVVLDWNYRWIHDANYN-
SCTV

NGGVNTTLCPDEATGSKNCFIEGVDYAASGVTANGSTLTLN-
QYMPSSSGGYT

SVSPRLYLLGPDGKYVMLKLNGQELSFDVDLSALPCGENASLYLSQM-
DENGG

ANQYNTAGANYGSGYCDAQCPVQTWRNGTLNTSGQGFCCNEMDILEGN-
SRAN

ALTPHSCNATACDSAGCGFNPYGSGYPNYFGPGGTVDTSKPFTIITQF-
NTDN

GSPSGNLVSITRKYRQNGVDIPSAKPGGDTISSCPSASTYGGLATMG-
KALSS

GMVLIFSIWNDNSQYMNWLDSGSAGPCSSTEGNPSNILANNPGTHVVYS-
NIR

WGDIGSTTNSTGGNPPPPPASSTTFSTTRRSSTSSSSPSCIQTHWGQCG-
GIG

YTGCKTCTSGTTCQYSNDYYSQCL*

SEQ ID NO: 8
SQQPGTSTPEVHPKLTTYKCTTSGGCVAQNTSVVLDWNYRWMHDANYN-
SCTV

NGGVNTTLCPDEATCGKNCFIEGVDYAASGVTASGSTLTLN-
QYMPSSSGGYS

SVSPRLYLLGPDGKYVMLKLNGQELSEDVDLSALPCGENASLYLSQM-
DENGG

ANQYNTAGANYGSGYCDAQCPVQTWRNGTLNTSGQGFCCNEMDILEGN-
SRAN

ALTPHSCNATACDSAGCGFNPYGSGYPNYFGPGGTVDTSKPFTIITQF-
NTDN

GSPSGNLVSITRKYRQNGVDIPSAKPGGDTISSCPSASAYGGLATMG-
KALSS

GMVLIFSIWNDNSQYMNWLDSGSAGPCSSTEGNPSNILANNPGTHVVYS-
NIR

WGDIGSTTNSTGGNPPPPPASSTTFSTTRRSSTTSSSPSCTQTHWGQCG-
GIG

YTGCKTCTSGTTCQYGNDYYSQCL*

SEQ ID NO: 9
SLQPGTSTPEVHPKLTTYKCTTSGGCVAQNTSVVLDWNYRWMHDANYN-
SCTV

NGGVNTTLCPDEATCCKNCFIEGVDYAASGVTASGSTLTLN-
QYMPSSSGGYS

SVSPRLYLLGPDGKYVMLKLNGQELSFDVDLSALPCGENASLYLSQM-
DENGG

ANQYNTAGANYGSGYCDAQCPVQTWRNGTLNTSGKGFCCNEMDILEGN-
SRAN

ALTPHSCNATACDSAGCGFNPYGSGYPNYFGPGGTVDTSKPFTIITQF-
NTDN

GSPSGNLVSITRKYRQNGVDIPSAKPGGDTISSCPSASAYGGLATMG-
KALSS

GMVLIFSIWNDNSQYMNWLDSGSAGPCSSTEGNPSNILANNPGTHVVYS-
NIR

WGDIGSTTNSTGGNPPPPPASSTTFSTTRRSSTTSSSPSCTQTHWGQCG-
GIG

YTGCKTCTSGTTCQYSNDYYSQCL*

SEQ ID NO: 10
SQQPGTSTPEVHPKLTTYKCTTSGGCVAQNTSVVLDWNYRWMHDANYN-
SCTV

NGGVNTTLCPDEATCGKNCFIEGVDYAASGVTASGSTLTLN-
QYMPSSSGGYS

SVSPRLYLLGPDGKYVMLKLNGQELSFDVDLSALPCGENASLYLSQM-
DENGG

ANQYNTAGANYGSYCDAQCPVQTWRNGTLNTSGQGFCCNEMDILEGN-
SRAN

ALTPHSCNATACDSAGCGFNPYKSGYPNYFGPGGTVDTSKPFTIITQF-
NTDN

GSPSGNLVSITRKYRQNGVDIPSAKPGGDTISSCPSASPYGGLATMG-
KALSE

GMVLIFSIWNDNSQYMNWLDSGSAGPCSSTEGNPSNILANNPGTHVVYS-
NIR

WGDIGSTTNSTGGNPPPPPASSTTFSTTRRSSTTSSSPSCTQTHWGQCG-
GIG

YTGCKTCTSGTTCQYGNDYYSQCL*

SEQ ID NO: 11
SQQPGTSTPEVHPKLTTYKCTTSGGCVAQNTSVVLDWNYRWMHDANYN-
SCTV

NGGVNTTLCPDEATCGKNCFIEGVDYAASGVTASGSTLTLN-
QYMPSSSGGYS

SVSPRLYLLGPDGKYVMLKLNGQELSFDVDLSALPCGENASLYLSQM-
DENGG

ANQYNTAGANYGSYCDAQCPVQTWRNGTLNTSGQGFCCNEMDILEGN-
SRAN

ALTPHSCNATACDSAGCGFNPYGSGYPNYFGPGGTVDTSKPFTIITQF-
NTDN

GSPSGNLVSITRKYRQNGVDIPSAKPGGDTISSCPSASAYGGLATMG-
KALSD

GMVLIFSIWNDNSQYMNWLDSGEACPCSSTEGNPSNILANNPGTHVVYS-
NIR

WGDIGSTTNSTGGNPPPPPASSTTFSTTRRSSTTSSSPSCTQTHWGQCG-
GIG

YTGCKTCTSGTTCQYGNDYYSQCL*

SEQ ID NO: 12
SQQPGTSTPEVHPKLTTYKCTTSGGCVAQNTSVVLDWNYRWMHDANYN-
SCTV

NGGVNTTLCPDEATCGKNCFIEGVDYAASGVTASGSTLTLN-
QYMPSSSGGYS

SVSPRLYLLGPDGKYVMLKLNGQELSFDVDLSALPCGENASLYLSQM-
DENGG

ANQYNTAGANYGSYCDAQCPVQTWRNGTLNTSGQGFCCNEMDILEGNS-
PAN

ALTPHSCNATACDSAGCGFNPYKSGYPNYFGPGGTVDTSKPFTIITQF-
NTDN

GSPSGNLVSITRKYRQNGVDIPSAKPGGDTISSCPSASAYGGLATMG-
KALSD

GMVLIFSIWNDNSQYMNWLDSGSAGPCSSTEGNPSNILANNPGTHVVYS-
NIR

WGDIGSTTNSTGGNPPPPPASSTTFSTTRRSSTTSSSPSCTQTHWGQCG-
GIG

YTGCKTCTSGTTCQYGNDYYSQCL*

SEQ ID NO: 13
SQQPGTSTPEVHPKLTTYKCTTSGGCVAQNTSVVLDWNYRWIHDANYN-
SCTV

NGGVNTTLCPDEATCSKNCFIEGVDYAASGVTANGSTLTLN-
QYMPSSSGGYS

SVSPRLYLLGPDGEYVMLKLNGQELSFDVDLSALPCGENGSLYLSQM-
DENGG

ANQYNTAGANYGSYCDAQCPVQTWRNGTLNTSGQGFCCNEMDILEGN-
SRAN

ALTPHSCTATACDSAGCGFNPYGSGYPNYFGPGDTVDTSKPFTIITQF-
NTDN

GSPSGNLVSITRKYPQNGVDIPSAKPGGDTISSCPSASAYGGLATMG-
KALSS

GMVLIFSIWNDNSQYMNWLDSGSAGPCSSTEGNPSNILANNPGTHVVYS-
NIR

WGDIGSTTNSTGGNPPPPPASSTTFSTTRRSSTTSSSPSCTQTHWGQCG-
GIG

YTGCKTCTSGTTCQYGNDYYSQCL*

SEQ ID NO: 14
SQQPGTSTPEVHPKLTTYKCTTSGGCVAQDTSVVLDWNYRWIHDANYN-
SCTV

NGGVNTTLCPDEATCGKNCFIEGVDYAASGVTANGSTLTLN-
QYMPSSSGGYS

SVSPRLYLLGPDGEYVMLKLNGQELSFDVDLSALPCGENGSLYLSQM-
DENGG

ANQYNTAGANYGSYCDAQCPVQTWRNGTLNTSGQGFCCNEMDILEGN-
SRAN

ALTPHSCTATACDSAGCGFNPYGSGYPNYFGPGDTVDTSKPFTIITQF-
NTDN

GSPSGNLVSITRKYRQNGVDIPSAKPGGDTISSCPSASAYGGLATMG-
KALSS

GMVLIFSIWNDNSQYMNWLDSGSAGPCSSTEGNPSNILANNPGTHVVYS-
NIR

WGDIGSTTNSTGGNPPPPPASSTTFSTTRRSSTTSSSPSCTQTHWGQCG-
GIG

YTGCKTCTSGTTCQYGNDYYSQCL*

SEQ ID NO: 15
atgagatttccttcaattttttactgcagtttttattcgcagcatcctccgcat tagctgctccagtcaacactacaacagaagatgaaacggcacaaattccggc tgaagctgtcatcggttacttagatttagaaggggatttcgatgttgctgtt ttgccattttccaacagcacaaataacgggttattgttttataaatactacta ttgccagcattgctgctaaagaagaaggggtatctttggataaacgtgaggc ggaaagcatgccaccaccaccaccactcctccggctctctgcagccagga acttctactccagaggtgcacccaaagctgaccacctacaagtgtac-
cacct ctggtggttgtgttgctcagaacacctatgttgttctggactggaacta-
cag atggatccacgacgccaactacaactcttgtaccgtgaacggtggtgt-
caac accactctgtgtccagacgaggctactggtagcaagaactgcttcatc-
gagg gtgttgactacgctgcttctggtgttactgccaatggttctaccttgac-
cct gaaccagtacatgccatcttcctctggcggttacacttctgtgtcgc-
caaga ctgtacttgttgggtccagacggtaagtacgttatgctgaagctgaacg-
gac aggagctgtcttttgacgttgacctgtctgctttgccatgtggaga-
gaacgc ttctctgtacctgtctcagatggacgagaacggtggagctaaccagta-
caac -continued

```
accgccggtgctaactacggttctggttactgtgacgccagtgtcca
gttc agacttggagaaacggaaccctgaacacttctggccagggattctgctg
taa cgagatggacatcttggagggaaactctagagctaacgctctgccccca
cac tcttgtaatgctaccgcttgtgactctgctggttgcggttttaaccat
acc gctcgggttacccaaactactttggcccaggtggcactgttgacacctc
gaa gccattcaccatcatcacccagttcaacaccgacaacggttctc
catctggt aacctggtgtcgatcaccagaaagtacagacagaacggcgctgacatc
ccat ccgctaaaccaggtggcgacaccatttcgtcttgtccatctgcctc
tactta cggtggattggctaccatgggaaaggctctgtccgagggaatggtgct
gatc ttctcgatctggaacgacaactcgcagtacatgaactggctggactctg
gtg atgctggtccatgttcttccaccgagggcaacccatctaacatcctg
gctaa caacctggtactcacgtggtgtactcgaacattagatggggcgacat
tggt tctaccaccaactctaccggtggtaacccaccaccaccacctgcatct
tcta ccaccttctcgaccgccagaagatcgtctacctcctcttcttctc
catcttg tatccagactcactggggtcagtgtggtggtattggctacaccggctg
taag acctgtacctctggaaccacttgccagtacagcaacgactac
tactctcagt gcctgtga
```

SEQ ID NO: 16:

```
atgtatcggaagttggccgtcatctcggccttcttggccacagcacgggctt ctctgcaaccgggtaccagcaccccgaggtccatcccaagttgacaac
cta caagtgtacaacctccgggggtgcgtggcccagaacacctatgtggtc
ctt gactggaactaccgctggatccacgacgcaaactacaactcgtgcac
cgtca acggcggcgtcaacaccacgctctgccctgacgaggcgaccggtag
caagaa ctgcttcatcgagggcgtcgactacgccgcctcgggcgtcacggc
caatggc agcaccctcaccctgaaccagtacatgcccagcagctctggcggcta
cacta gcgtctctcctcggctgtatctcctgggtccagacggtaagtacgtgat
gct gaagctcaacggccaggagctgagcttcgacgtcgacctctctgctct
gccg tgtggagagaacgcctcgctctacctgtctcagatggacga
gaacggggcg ccaaccagtataacacggccggtgccaactacgggagcggctactgc
gatgc tcagtgccccgtccagacatggaggaacggcaccctcaacactagcggc
cag
```

-continued

```
ggcttctgctgcaacgagatggatatcctggagggcaactcgagggc
gaatg ccttgacccctcactcttgcaatgccacggcctgcgactctgccggtt
gcgg cttcaaccctatcgcagcggctacccaaactacttcggccccggag
gcacc gttgacacctccaagccattcaccatcatcacccagttcaacacgga
caacg gctcgccctcgggcaaccttgtgagcatcacccgcaagtacaga
caaaacgg cgtcgacatcccagcgccaaaccggcggcgacaccatctcgtcctgc
ccg tccgcctcaacttacggcggcctcgccaccatgggcaaggccctgagc
gagg gcatggtgctcatcttcagcatttggaacgacaacagccagtacat
gaactg gctcgacagcggcgatgccggcccctgcagcagcaccgagggcaac
ccatcc aacatcctggccaacaacccccggtacgcacgtcgtctactccaacatc
cgct ggggagacattgggtctactacgaactcgactggtggtccgcccccgc
ctgc gtccagcacgacgttttcgactgcccggaggagctcgacgtcctc
gagcagc ccgagctgcatccagactcactgggggcagtgcggtggcattgggta
caccg ggtgcaagacgtgcacgtcgggcactacgtgccagtatagcaacgac
tacta ctcgcaatgcctttaa
```

EXAMPLES

Example 1: Generation of Libraries and Specific Variants

A library based on Seq. ID NO: 3 ("N7" library) was produced using SEQ ID NO: 3 as template by error-prone PCR using Taq polymerase following the literature protocol (Joyce et al) using PCR conditions as follows: 2 min at 95° C., 30 cycles of (1 min at 95° C., 1 min at 56° C., 1 min at 72° C.), 5 min at 72° C. All products obtained from PCRs were purified with the QIAquick PCR Purification Kit (Qiagen, Hilden, Germany).

Specific variants of Seq. ID NO: 3 were prepared by a modified PCR protocol using primers containing the mutated nucleotide sequence (Ho, S. N. et al. Gene; 1989; 77; 51-9).

Example 2: Expression in *Pichia pastoris*

Linear Expression Cassette (LEC) Construction—

LECs (Liu Z, et al. Chembiochem. 2008 Jan. 4; 9 (1):58-61) with Zeocin marker and the GAP promoter were constructed by a modified PCR protocol.

*Pichia pastoris* Transformation and Cultivation—

Competent cells were prepared and transformed as described (Lin-Cereghino, J., et al. *BioTechniques*. 2005, 38, 44-48). Transformants were selected on YPD agar plates containing Zeocin 100 mg/L, and picked to deepwell plates (DWP) (BMD5% 250 ml/well) by picking robot (QPix2, Genetix). Inoculated DWPs were cultivated for 60 h at 28° C., 80% humidity, and 280 rpm.

Example 3: Expression in *Trichoderma reesei*

*Trichoderma reesei* Expression Vector Construct

Figure 2:
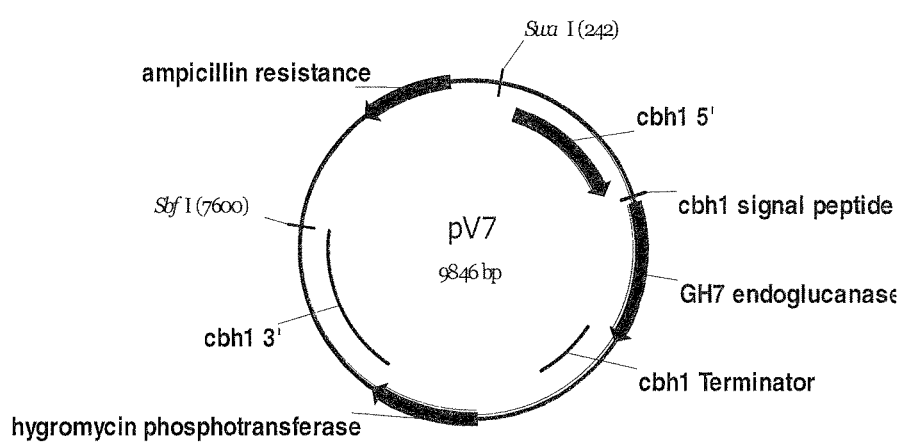
FIG. 2: *Trichoderma reesei* expression plasmid. The DNA sequence coding for the mature endoglucanase gene is cloned in fusion to the TrCBHI signal peptide sequence under control of the TrCBHI promoter. The SwaI/SbfI excisable expression cassette contains a hygromycine resistance cassette for selection of transformants.

SbfI/SwaI digested linearized pV7 plasmid (FIG. 2) DNA was transformed into *Trichoderma reesei* SCF41 essentially as described by Penttilä et al 1997. Selection of transformants was done on Mandel's Andreotti media plates containing hygromycine as selective agent (100 mg/l). Transformants were verified by PCR.

Example 4: Determination of Substrate Conversion Capacity at Different Temperatures for Indication of the Thermostability of Seq ID NO. 2-Variants Using 4-Methylumbellifery-β-D-Cellobiosid (4-MUC)

For precise comparison of the thermal stability 10 µl of the *Pichia pastoris* culture supernatants containing the secreted endoglucanase variants were incubated with 90 µl of 100 µM 4-MUC (dissolved in sodium acetate buffer (50 mM, pH 5.0)) in the temperature gradient of an Eppendorff Gradient Thermocycler. 24 reaction mixtures were incubated in a temperature gradient reaching from 45° C. to 65° C. and from 55° C. to 75° C. (each reaction was held at a unique constant temperature level) for one hour. The enzymatic activity at the respective temperature could be determined after addition of 100 µl 1M sodium carbonate solution to each reaction and measurement of the fluorescence intensity at 360 nm/454 nm in a Tecan Infinite M200 plate reader. For comparison of the thermostability the fluorescence counts of each temperature point, the relative enzymatic activity was determined by dividing by the maximum count of a series (normalization to 1). The temperature profile for any given enzyme was generated by plotting the relative enzymatic activity over the measured temperature range.

Example 5: Active Thermostabilization of Some Endoglucanase Variants

This example describes examples of the surprising effect of active thermostabilization. In this example proteins (culture supernatant) (Table 5 below) expressed in *Pichia pastoris* were used.

FIG. 3 demonstrates the determined properties of the proteins of the invention: proteins designated as [1], [4], [5], [7], [8], [9] and [10] show active thermostabilization and temperature stability, while proteins designated as [3] and [6] show temperature stability, but not active thermostabilization.

TABLE 5

Proteins tested in Example 5, 6 and 7 Designation

| | SEQ ID NO: | FIG. No. | Mutations with respect to Seq. ID NO2 |
|---|---|---|---|
| *Hypocrea pseudoconingii* EGI | SEQ. ID NO: 4 | [2] | L2Q, N30D, Y32S, I42M, G67C, S68G, N86S, T104S, K118E, A144G, N216T, R231G, G242D, T299A, E312S, D335S, A392T, S398T, I405T, S432G |
| Variant of *Hypocrea pseudokoningii* EGI (E153K with respect to Seq. ID NO: 4) | Seq. ID NO: 5 | [3] | L2Q, N30D, Y32S, I42M, G67C, S68G, N86S, T104S, K118E, A144G, E153K, N216T, R231G, G242D, T299A, E312S, D335S, A392T, S398T, I405T, S432G |
| EG/variant of the invention; derived by mutagenesis from *Hypocrea pseudokoningii* EGI sequence | Seq. ID NO: 2 | [1] | |
| Example Variant 1 of Seq. ID NO: 2 | Seq. ID NO: 6 | [4] | Y32S, I42M, S68G, N86S, T104S, R231G, E312S, D335S, A392T |
| Example Variant 2 of Seq. ID NO: 2 | Seq. ID NO: 7 | [5] | R231G, E312S, D335S, A392T |
| Variant of *Hypocrea pseudokoningii* EGI (with respect to Seq. ID NO: 4) | Seq. ID NO: 8 | [6] | , L2Q, Y32S, I42M, G67C, S68G, N86S, T104S, R231G, T299A, E312S, D335S, A392T, S398T, I405T, S432G |
| Example Variant 3 of Seq. ID NO: 2 | Seq. ID No: 9 | [7] | , Y32S, I42M, G67C, S68C, N86S, T104S, Q191K, R231G, T299A, E312S, D335S, A392T, S398T, I405T |
| Example Variant 4 of Seq. ID NO: 2 | Seq. ID No: 10 | [8] | , L2Q, Y32S, I42M, G67C, S68G, N86S, T104S, R231K, T299A, D335S, A392T, S398T, I405T, S432G |
| Example Variant 5 of Seq. ID NO: 2 | Seq. ID No: 11 | [9] | , L2Q, Y32S, I42M, G67C, S68G, N86S, T104S, R231G, T299A, E312D, D335E, A392T, S398T, I405T, S432G |
| Example Variant 6 of Seq. ID NO: 2 | Seq. ID NO: 12 | [10] | , L2Q, Y32S, I42M, G67C, S68G, N86S, T104S, R231K, T299A, E312D, D335S, A392T, S398T, I405T, S432G |
| Example Variant 7 of Seq. ID No: 2 | Seq. ID NO: 13 | | , L2Q, N30D, Y32S, G67C, T104S, K118E, A144G, N216T, R231G, G242D, T299A, E312S, D335S, A392T, S398T, I405T, S432G |
| Example Variant 8 of Seq. ID No: 2 | Seq. ID NO: 14 | | , L2Q, N30D, Y32S, G67C, S68G, T104S, K118E, A144G, N216T, R231G, G242D, T299A, E312S, D335S, A392T, S398T, I405T, S432G |

Example 6: Determination of Reducing Sugar Release on Straw

The release of reducing sugar on straw was determined by applying acid pretreated wheat straw with a dry matter of 2.5%. The following enzymes were added to the reaction mixture: cellobiohydrolase I (12.5 mg/l), beta-glucosidase (40 CBU/mg cellobiohydrolase I) and the tested GH7 endoglucanase variant (12.5 mg/l). The straw hydrolysis was incubated at 60° C. by continuous shaking for 48 h.

Example 7: Determination of the Temperature Profile of Seq ID. No 2 Variants

Figure 5:
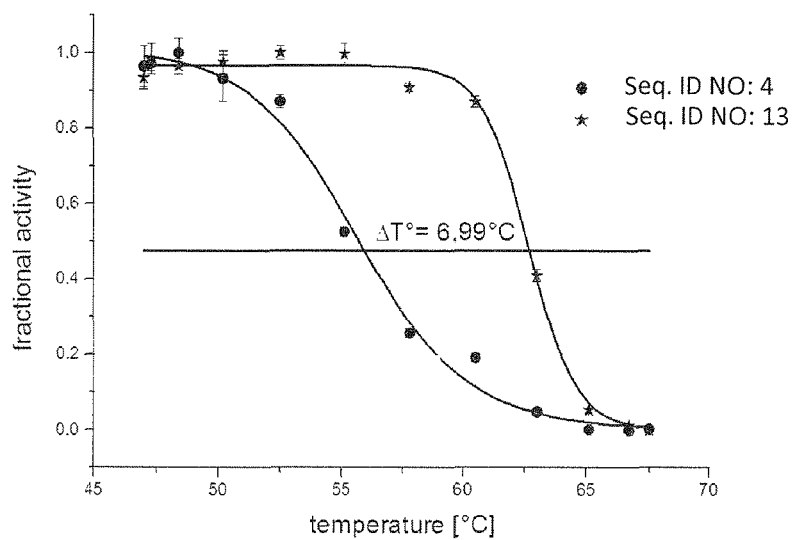
FIG. 5: Thermal stabilization of Seq. ID NO: 13 compared to Seq. ID NO: 4
Figure 6:
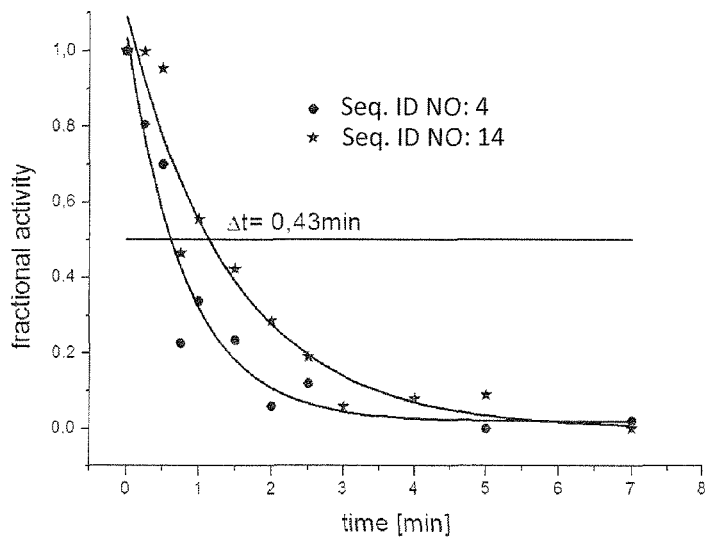
FIG. 6: Determination of half-lives at 70° C. (Example 7) for Seq. ID NO: 14 compared to Seq. ID NO: 4.

For the MUL (4-methylumbellyferryl β-D-lactopyranoside) activity assay, 10 µl of the cultivation supernatant was mixed with 90 µl 100 µM MUL in 25 mM Na-acetate buffer with pH 4.8. Plates were sealed and incubated for 2 h, with 300 rpm shaking, at 45° C. and 59° C. each (for rescreening also at 65° C.) Reaction was quenched by adding 100 µl Na$_2$CO$_3$ per well. Excitation was performed at 365 nm, and fluorescence measured at 450 nm. The results are shown in FIG. 5.

Example 8: Determination of the Temperature Profile of Seq ID. No 2 Variants

The half-lives of the enzymes were determined by measuring the residual activity using the MUL assay described in Example 7 after incubation of expression supernatants of *Pichia pastoris* cultures at 70° C. for 0 to 7 min in a water bath. Samples were put on ice after the precise incubation period before setup of the activity assay.

The invention claimed is:

1. A protein having endoglucanase activity and at least 99.5% identity to SEQ. ID. NO.: 2.

2. The protein according to claim 1, wherein the protein shows at least 90% residual substrate conversion capacity at temperature 60° C. when incubation is done for one hour.

3. A protein having at least 99.5% identity to SEQ. ID. NO.: 2, said protein having endoglucanase activity, wherein said protein belongs to the GH7 class and shows active thermostabilization.

4. A mixture containing the protein according to claim 1 and one or more enzyme(s), wherein said enzymes are cellulases, hemi-cellulases or pectinases.

5. A protein consisting of the amino acid sequence of SEQ. ID. NO.: 2 and having endoglucanase activity.

6. The protein according to claim 5, wherein the protein shows at least 90% residual substrate conversion capacity at temperature 60° C. when incubation is done for one hour.

7. The protein according to claim 5, wherein said protein belongs to the GH7 class and shows active thermostabilization.

8. A mixture containing the protein according to claim 5 and one or more enzyme(s), wherein said enzymes are cellulases, hemi-cellulases or pectinases.

9. The protein according to claim 3, wherein the protein shows at least 90% residual substrate conversion capacity at temperature 60° C. when incubation is done for one hour.

10. A mixture containing the protein according to claim 3 and one or more enzyme(s), wherein said enzymes are cellulases, hemi-cellulases or pectinases.

* * * * *